United States Patent
Mendelsohn et al.

(10) Patent No.: US 7,122,655 B2
(45) Date of Patent: Oct. 17, 2006

(54) COMPOSITIONS INVOLVING M-RIP, AND RELATED METHODS FOR SCREENING FOR ANTI-HYPERTENSIVE AGENTS, AND USES THEREOF

(75) Inventors: Michael E. Mendelsohn, Wellesley, MA (US); Howard K. Surks, Newton, MA (US)

(73) Assignee: New England Medical Center Hospital, Inc., Boston, MA (US)

( * ) Notice: Subject to any disclaimer, the term of this patent is extended or adjusted under 35 U.S.C. 154(b) by 112 days.

(21) Appl. No.: 10/715,632

(22) Filed: Nov. 17, 2003

(65) Prior Publication Data

US 2004/0180811 A1      Sep. 16, 2004

Related U.S. Application Data

(60) Provisional application No. 60/426,591, filed on Nov. 15, 2002.

(51) Int. Cl.
*A61K 38/16* (2006.01)
*C07H 21/04* (2006.01)
*C12N 9/16* (2006.01)

(52) U.S. Cl. .............. 536/23.5; 435/19; 435/69.1; 435/6; 435/320.1; 435/325; 435/196; 514/7; 514/929; 514/930; 536/23.2

(58) Field of Classification Search .............. 435/196, 435/19, 6, 69.1, 320.1, 325; 536/23.5
See application file for complete search history.

(56) References Cited

OTHER PUBLICATIONS

Surk's H.K., Richards, C.T. and Mendelsoon M.E. Myosin Phosphatase Rho-interacting protein: New members of the myosin phosphatase complex that directly bins RhoA. J. Biolo. Chem. 278 (51), 51484-51493 (2003).*

Inazawa et al., Cloning of human orthologue RHOIP3 of Mus Rhoip3, GenBank accession No. AB098507 (Jun. 21, 2003).*

Ottenwaelder et al., GeneBank submission AL834513 Jul. 12, 2002.*

Yue H. et al., Human intracellular signaling molecules INTSIG-24 cDNA. ADA13387 with a provisional filing date of Sep. 14, 2001 (2001US-0322188P) sequence No.: 17.*

Diekmann et al., "In Vitro Binding Assay for Interactions of Rho and Rac with GTPase-Activating Proteins and Effectors," *Methods Enzymol*, 256:207-215 (1995).

Gebbink et al., "Identification of a Novel, Putative Rho-Specific GDP/GTP Exchange Factor and a RhoA-Binding Protein: Control of Neuronal Morphology," *J. Cell Biol*. 137:1603-1613 (1997).

Mulder et al., "p116$^{Rip}$ is a Novel Filamentous Actin-Binding Protein," *J. Biol. Chem.* 278:27216-27223 (2003).

Surks et al., "Myosin Phosphatase-Rho Interacting Protein. A New Member of Myosin Phosphatase Complex That Directly Binds RhoA," *J. Biol. Chem.* 278:51484-51493 (2003).

* cited by examiner

*Primary Examiner*—Rebecca E. Prouty
*Assistant Examiner*—Kagnew Gebreyesus
(74) *Attorney, Agent, or Firm*—Clark & Elbing LLP

(57) ABSTRACT

The present invention relates to screening methods that make use of Myosin Phosphatase-Rho interacting Protein (M-RIP) for the identification of novel therapeutics for hypertension and hypertensive conditions. Also disclosed are methods for treating or preventing hypertension or hypertensive conditions by administering to a mammal a therapeutically effective amount of an agent that reduces the level or activity of M-RIP. According to this invention, the agent decreases contractile and increases relaxant effects of smooth muscle cells, ultimately decreasing the systemic blood pressure of a mammal. For example, the agent may reduce binding of M-RIP to myosin phosphatase, RhoA, or both.

4 Claims, 26 Drawing Sheets

Figure 1A
PAGE 1 of 2

```
Human:    1  MSAAKENPCRKFQANIFNKSKCQNCFKPREPHLLNDEDLTQAKPIYGGWLLLAPDGTDFD  60
             MSAAKENPCRKFQANIFNKSKCQNCFKPRE HLLNDEDLTQAKPIYGGWLLLAPDGTDFD
Mouse:    1  MSAAKENPCRKFQANIFNKSKCQNCFKPRESHLLNDEDLTQAKPIYGGWLLLAPDGTDFD  60

Figure 1A
PAGE 2 of 2

```
Human:  837  AQALEAERQALRQCQRENQELNAHNQELNNRLAAEITRLRTLLTGDGGGEATGSPLAQGK  896
              AQALEAERQALRQCQRENQELNAHNQELNNRLAAEITRLRTLLTGDGGE+TG PL QGK
Mouse:  837  AQALEAERQALRQCQRENQELNAHNQELNNRLAAEITRLRTLLTGDGGGESTGLPLTQGK  896

FIGURE 1C

SEQ ID NO: 19

```
ATGTCGGCAGCCAAGGAGAACCCGTGCAGGAAATTCCAGGCCAACATCTTCAACAAGAGCAAGTGTCAG
AACTGCTTCAAGCCCCGCGAGCCGCATCTGCTCAACGACGAGGACCTGACGCAGGCAAAACCCATTTAT
GGCGGTTGGCTGCTCCTGGCTCCAGATGGGACCGACTTTGACAACCCAGTGCACCGGTCTCGGAAATGG
CAGCGACGGTTCTTCATCCTTTACGAGCACGGCCTCTTGCGCTACGCCCTGGATGAGATGCCCACGACC
CTTCCTCAGGGCACCATCAACATGAACCAGTGCACAGATGTGGTGGATGGGGAGGGCCGCACGGGCCAG
AAGTTCTCCCTGTGTATTCTGACGCCTGAGAAGGAGCATTTCATCCGGGCGGAGACCAAGGAGATCGTC
AGTGGGTGGCTGGAGATGCTCATGGTCTATCCCCGGACCAACAAGCAGAATCAGAAGAAGAAACGGAAA
GTGGAGCCCCCACACCACAGGAGCCTGGGCCTGCCAAGGTGGCTGTTACCAGCAGCAGCAGCAGCAGC
AGCAGCAGCAGCATCCCCAGTGCTGAGAAAGTCCCCACCACCAAGTCCACACTCTGGCAGGAAGAAATG
AGGACCAAGGACCAGCCAGATGGCAGCAGCCTGAGTCCAGCTCAGAGTCCCAGCCAGAGCCAGCCTCCT
GCTGCCAGCTCCCTGCGGGAACCTGGGCTAGAGAGCAAAGAAGAGGAGAGCGCCATGAGTAGCGACCGC
ATGGACTGTGGCCGCAAAGTCCGGGTGGAGAGCGGCTACTTCTCTCTGGAGAAGACCAAACAGGACTTG
AAGGCTGAAGAACAGCAGCTGCCCCCGCCGCTCTCCCTCCCAGCCCCAGCACCCCCAACCACAGGAGG
TCCCAGGTGATTGAAAAGTTTGAGGCCTTGGACATTGAGAAGGCAGAGCACATGGAGACCAATGCAGTG
GGGCCCTCACCATCCAGCGACACACGCCAGGGCCGCAGCGAGAAGAGGGCGTTCCCTAGGAAGCGGGAC
TTCACCAATGAAGCCCCCCAGCTCCTCTCCCAGACGCCTCGGCTTCCCCCCTGTCTCCACACCGAAGA
GCCAAGTCACTGGACAGGAGGTCCACGGAGCCCTCCGTGACGCCCGACCTGCTGAATTTCAAGAAAGGC
TGGCTGACTAAGCAGTATGAGGACGGCCAGTGGAAGAAACACTGGTTTGTCCTCGCCGATCAAAGCCTG
AGATACTACAGGGATTCAGTGGCTGAGGAGGCAGCCGACTTGGATGGAGAAATTGACTTGTCCGCATGT
TACGATGTCACAGAGTATCCAGTCCAGAGAAACTATGGCTTCCAGATACATACAAAGGAGGGCGAGTTT
ACCCTGTCGGCCATGACATCTGGGATTCGGCGGAACTGGATCCAGACCATCATGAAGCACGTGCACCCG
ACCACTGCCCCGGATGTGACCAGCTCGTTGCCAGAGGAAAAAAACAAGAGCAGCTGCTCTTTTGAGACC
TGCCCGAGGCCTACTGAGAAGCAAGAGGCAGAGCTGGGGGAGCCGGACCCTGAGCAGAAGACGAGCCGC
GCACGGGAGCGGAGGCGAGAGGGCCGCTCCAAGACCTTTGACTGGGCTGAGTTCCGTCCCATCCAGCAG
GCCCTGGCTCAGGAGCGGGTGGGCGGCGTGGGCCTGCTGACACCCACGAGCCCCTGCGCCCTGAGGCG
GAGTCTGGGGAGCTGGAGCGGGAGCGTGCACGGAGGCGGGAGGAGCGCCGCAAGCGCTTCGGGATGCTC
GACGCCACAGACGGGCCAGGCACTGAGGATGCAGCCCTGCGCATGGAGGTGGACCGGAGCCCAGGGCTG
CCTATGAGCGACCTCAAAACGCATAACGTCCACGTGGAGATTGAGCAGCGGTGGCATCAGGTGGAGACC
ACACCTCTCCGGGAAGAGAAGCAGGTGCCCATCGCCCCGTCCACCTGTCTTCTGAAGATGGGGGTGAC
CGGCTCTCCACACACGAGCTGACCTCTCTGCTCGAGAAGGAGCTGGAGCAGAGCCAGAAGGAGGCCTCA
GACCTTCTGGAGCAGAACCGGCTCCTGCAGGACCAGCTGAGGGTGGCCCTGGGCCGGGAGCAGAGCGCC
CGTGAGGGCTACGTGCTGCAGGCCACGTGCGAGCGAGGGTTTGCAGCAATGGAAGAAACGCACCAGAAG
AAGATTGAAGATCTCCAGAGGCAGCACCAGCGGGAGCTAGAGAAACTTCGAGAAGAGAAAGACCGCCTC
CTAGCCGAGGAGACAGCGGCCACCATCTCAGCCATCGAAGCCATGAAGAACGCCCACCGGGAGGAAATG
GAGCGGGAGCTGGAGAAGAGCCAGCGGTCCCAGATCAGCAGCGTCAACTCGGATGTTGAGGCCCTGCGG
CGCCAGTACCTGGAGGAGCTGCAGTCGGTGCAGCGGGAACTGGAGGTCCTCTCGGAGCAGTACTCGCAG
AAGTGCCTGGAGAATGCCCATCTGGCCCAGGCGCTGGAGGCCGAGCGGCAGGCCCTGCGGCAGTGCCAG
CGTGAGAACCAGGAGCTCAATGCCCACAACCAGGAGCTGAACAACCGCCTGGCTGCAGAGATCACACGG
TTGCGGACGCTGCTGACTGGGGACGGCGGTGGGGAGGCCACTGGGTCACCCCTTGCACAGGGCAAGGAT
GCCTATGAACTAGAGGTCTTATTGCGGGTAAAGGAATCGGAAATACAGTACCTGAAACAGGAGATTAGC
TCCCTCAAGGATGAGCTGCAGACGGCACTGCGGGACAAGAAGTACGAAGTGACAAGTACAAAGACATC
TACACAGAGCTCAGCATCGCGAAGGCTAAGGCTGACTGTGACATCAGCAGGTTGAAGGAGCAGCTCAAG
GCTGCAACGGAAGCACTGGGGGAGAAGTCCCCTGACAGTGCCACGGTGTCCGGATATGATATAATGAAA
TCTAAAAGCAACCCTGACTTCTTGAAGAAAGACAGATCCTGTGTCACCCGGCAACTCAGAAACATCAGG
TCCAAGTCCGTAATTGAGCAGGTCTCGTGGGATACCTGA
```

Figure 4C

| Amino Acids | MBS Binding |
|---|---|
| 672-707 (CC1) | - |
| 728-878 (CC2) | + |
| 900-974 (CC3) | - |
| 545-823 | - |
| 545-878 | + |

Figure 6B, top
| Phalloidin | M-RIP |
 

Figure 6B, middle
Phalloidin    MBS
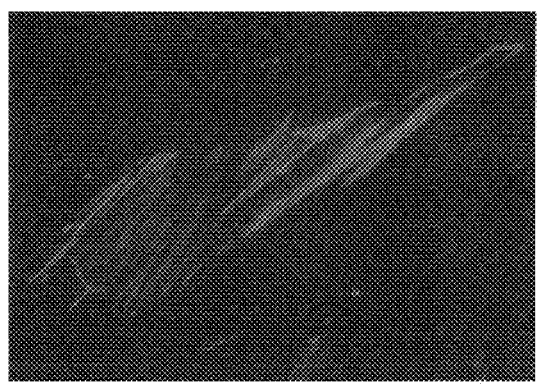
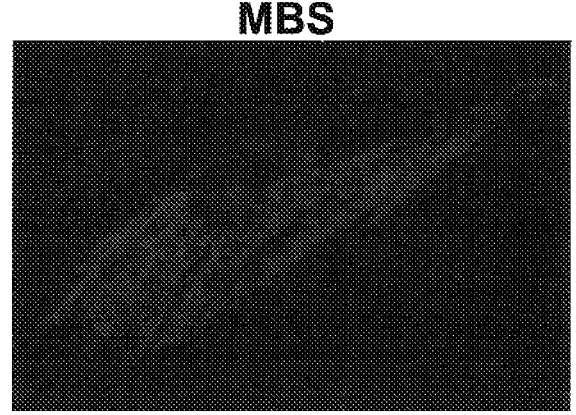

Figure 6B, bottom
Phalloidin
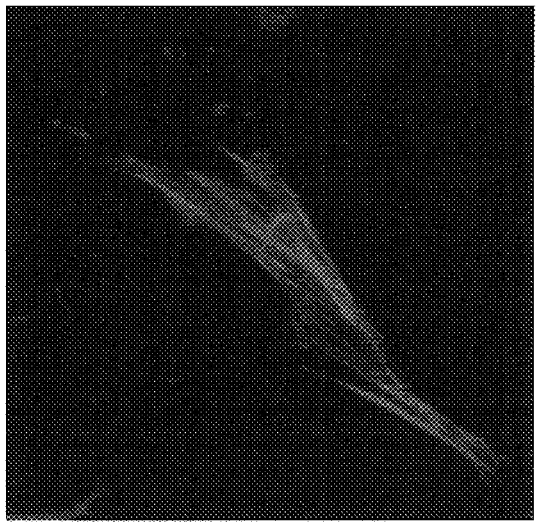
RhoA

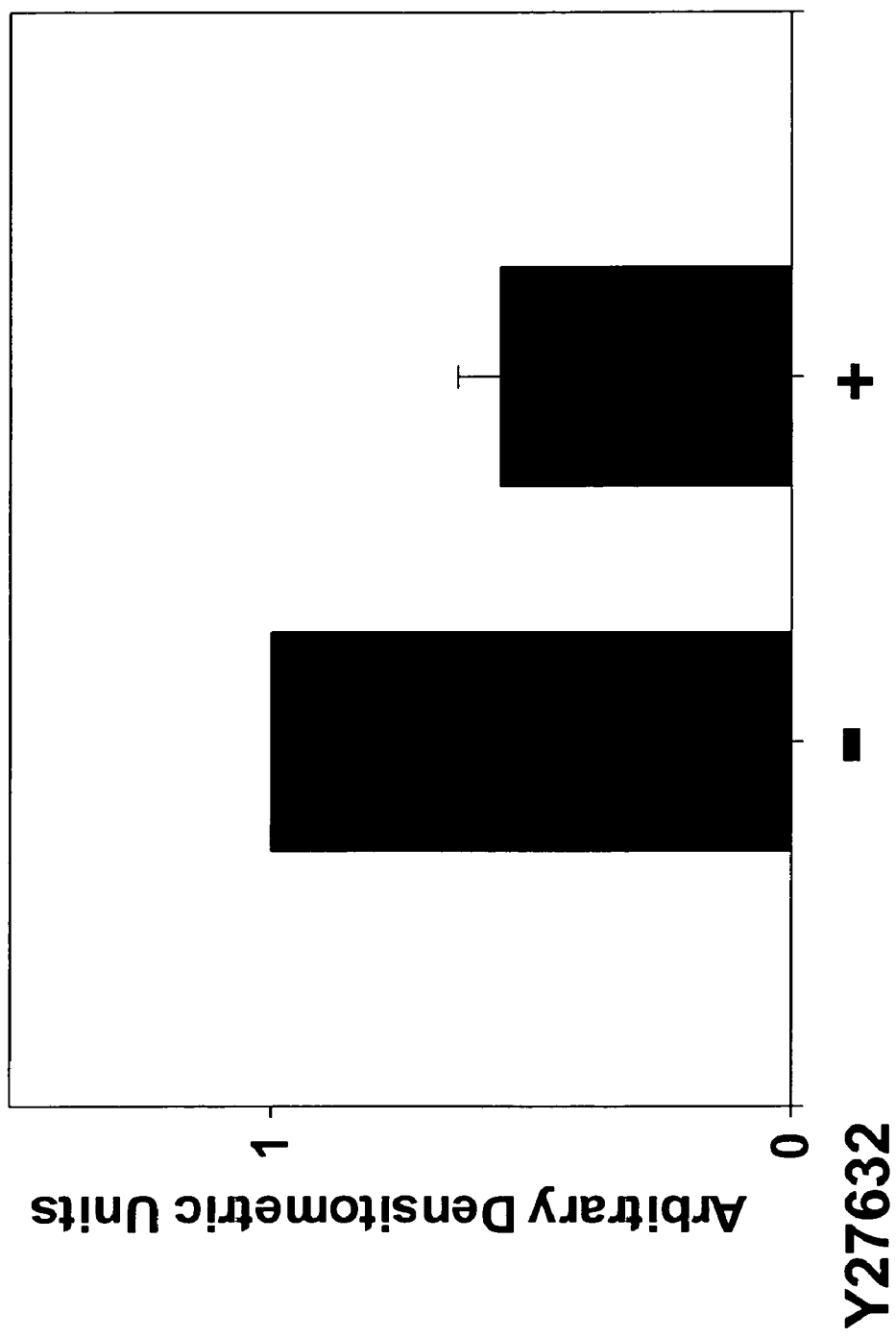

COMPOSITIONS INVOLVING M-RIP, AND RELATED METHODS FOR SCREENING FOR ANTI-HYPERTENSIVE AGENTS, AND USES THEREOF

CROSS REFERENCE TO RELATED APPLICATIONS

This application claims the benefit of the filing date of U.S. provisional application, U.S. Ser. No. 60/426,591, filed Nov. 15, 2002.

FIELD OF THE INVENTION

In general, the present invention involves the treatment, prevention, and reduction of hypertensive conditions. In particular, the invention relates to methods for identifying candidate compounds useful for treating or preventing hypertensive conditions. Further, methods are provided for preventing or reducing hypertension.

BACKGROUND OF THE INVENTION

Hypertension, a state characterized by the elevation of arterial blood pressure, is a widespread problem in developed countries. Although the etiology of this condition has yet to be clearly defined, a number of factors, both genetic and environmental, have been implicated as causal agents. Such factors include, for example, family history, salt intake, obesity, age, race, sex, stress, diet, smoking, serum cholesterol, and glucose intolerance. In certain cases, hypertension can also develop as a consequence of other disorders, such as Cushing's syndrome.

The repercussions of hypertension are diverse and, if untreated, hypertension often leads to premature death. Since elevated blood pressure imposes an increased workload on the heart, hypertensive patients often suffer from various cardiovascular disorders, such as angina pectoris, cardiac hypertrophy, coronary vascular diseases, ischemic heart injury, and, in more severe cases, myocardial infarction and heart failure. In addition, hypertension is often concomitant with the development of renal disorders and the occurrence of cerebrovascular conditions, such as cerebral infarction, cerebral hemorrhage, and subarachnoid hemorrhage. Reducing arterial blood pressure is thus critical in the prevention and even the treatment of such life-threatening conditions.

Various therapeutic strategies, including the administration of beta-blockers and vasodilators for example, have been designed for the treatment of hypertension and its associated complications. Though such modalities are generally effective in reducing blood pressure in patients, they are frequently associated with serious debilitating side effects, such as potassium depletion, hyperglycemia, depression, carbohydrate intolerance, tachychardia, allergic skin rashes, and in more severe cases vomiting, fever, diarrhea, angina, and cardiac failure. These drugs are therefore only administered to patients who suffer from severe cases of hypertension. In less serious cases, adoption of a healthier lifestyle is often recommended. Such lifestyle changes or therapies include dietary improvements or supplementation, stress reduction, physical exercise, and restriction of both alcohol consumption and smoking. While this latter strategy is generally safe and free from substantial side effects, the efficacy of lifestyle changes is variable and highly dependent on the patient's compliance. Furthermore, the anti-hypertensive effects provided by lifestyle improvements are rarely sufficient, particularly in moderate or severe cases of hypertension.

Thus, additional therapeutic modalities for reducing or preventing hypertension and its associated conditions are desirable.

SUMMARY OF THE INVENTION

In general, the invention provides compositions containing myosin phosphatase-Rho interacting protein (M-RIP), screening methods based on this protein or its nucleic acid coding sequence to identify anti-hypertensive agents, and uses of those agents for treating hypertensive conditions.

Accordingly, in a first aspect, the invention features a substantially pure polypeptide having at least 95%, 98%, 99%, or 100% sequence identity with the amino acid sequence of M-RIP protein (e.g., human or mouse). The amino acid sequence of the M-RIP protein is preferably substantially identical to SEQ ID NO: 1. Desirably, the polypeptide of the invention binds myosin phosphatase, RhoA, or both.

The invention also features a substantially pure nucleic acid molecule having at least 90%, 95%, 98%, 99%, or 100% sequence identity to the nucleic acid sequence of the M-RIP polynucleotide (SEQ ID NO: 19). The M-RIP polynucleotide may encode a human M-RIP protein. Desirably, the nucleic acid molecule of the invention encodes a polypeptide having an amino acid sequence substantially identical to SEQ ID NO: 1. Even more desirably, the nucleic acid encodes a polypeptide that binds myosin phosphatsase, RhoA, or both.

In another aspect, the invention provides methods for identifying a candidate compound for treating, reducing, or preventing hypertension or a hypertensive condition in a mammal. These methods involve the steps of: (a) contacting a cell expressing an M-RIP gene with a candidate compound; and (b) measuring M-RIP gene expression or M-RIP protein activity in the cell. A candidate compound that decreases the expression or the activity of M-RIP, relative to M-RIP expression or activity in a cell not contacted with the candidate compound, is identified as a candidate compound useful for treating, reducing, or preventing hypertension or a hypertensive condition in a mammal. For example, the candidate compound may reduce binding of M-RIP to myosin phosphatase, RhoA, or both.

In preferred embodiments, the M-RIP gene is an M-RIP fusion gene and the M-RIP-expressing cell is a mammalian cell (e.g., a rodent cell). In other embodiments, step (b) involves the measurement of M-RIP mRNA or protein.

In a related aspect, the invention provides methods for identifying a candidate compound for treating, reducing, or preventing hypertension or a hypertensive condition in a mammal. These methods involve the steps of: (a) contacting an M-RIP protein with a candidate compound; and (b) determining whether the candidate compound binds the M-RIP protein and/or decreases M-RIP activity. Candidate compounds that bind and decrease M-RIP activity are identified as candidate compounds useful for treating, reducing, or preventing hypertension or a hypertensive condition, in a mammal. Preferably, the candidate compound reduces binding of M-RIP to myosin phosphatase, RhoA, or both.

In yet another related aspect, the invention provides methods for identifying a candidate compound for treating, reducing, or preventing hypertension or a hypertensive condition in a mammal. These methods involve the steps of: (a) contacting an M-RIP protein (e.g., human M-RIP protein)

with a candidate compound; and (b) determining whether the candidate compound decreases binding of M-RIP to myosin phosphatase, RhoA, or both. Candidate compounds that decrease such binding are identified as candidate compounds useful for treating, reducing, or preventing hypertension or a hypertensive condition, in a mammal.

In preferred embodiments, these methods also test the ability of the candidate compound to decrease the expression of the M-RIP gene in a cell, for example a mammalian cell such as a rodent or human cell. Most preferably, the M-RIP is human M-RIP.

In another aspect, the present invention also features methods for treating, reducing, or preventing hypertension or a hypertensive condition in a mammal, as well as providing methods and compositions for identifying new candidate compounds for treating these disorders.

Accordingly, the invention features a method for treating, reducing, or preventing hypertension or a hypertensive condition in a mammal by administering to the mammal a pharmaceutical composition containing a therapeutic agent that reduces the level or activity of myosin phosphatase-Rho interacting protein (M-RIP) in an amount sufficient to treat, reduce, or prevent hypertension or a hypertensive condition. Although the expression of M-RIP is preferably reduced in vascular smooth muscles cells, such expression may also be reduced in other cells in the mammal. Desirably, the agent of the invention reduces the level or activity of M-RIP by at least 10%, 20%, 305, 40%, 50%, 60%, 70%, 80%, 90%, 95%, or even 100% below untreated control levels. For example, the agent may reduce binding of M-RIP to myosin phosphatase, RhoA, or both. Alternatively, the agent of the invention increases the activity of myosin phosphatase by at least 10%, 20%, 30%, 40%, 50%, 60%, 70%, 80%, 90%, 95%, 100%, or more than 100% above untreated levels. Following the administration of this agent, smooth muscle cell contraction is decreased by at least 10%, 20%, 305, 40%, 50%, 60%, 70%, 80%, 90%, 95%, or even 100% below untreated control levels such that hypertension or the hypertensive condition is treated, prevented, or reduced.

In all foregoing aspects of this invention, the mammal being treated is preferably a human. Typically, hypertensive conditions treated according to the present invention are cardiovascular (e.g., angina pectoris, ischemic heart disease, cardiac hypertrophy, myocardial infarction, coronary artery disease, congestive heart failure, vascular injury, blood vessel spasm, myocardial ischemia, or aortic aneurysm), cerebrovascular (e.g., cerebral infarction, cerebral hemorrhage, brain damage, loss of vision, or subarachnoid hemorrhage), or renal (e.g., renal failure, or end-stage renal disease).

Optionally, the mammal administered with the agent that reduces the level or activity of M-RIP may also receive a second therapeutic regimen, which may include a therapeutic agent. According to this invention, examples of second therapeutic agents include diuretics (e.g., chlorthalidone, furosemide, hydrochlorothiazide, indapamide, metotazone, amiloride, spironolactone, or triamterene), beta-blockers (e.g., acebutolol, amlodipine, amiodarone, atenolol, betaxolol, bisoprolol fumarate, carterolol hydrochloride, metoprolol, mexiletine, moricizine, nadolol, penbutolol, pindolol, procainamide, propranodlol, or timolol), sympathetic nerve inhibitors (e.g., guanabenz, guanfacine, guanadrel, midodrine, or primidone), vasodilators (e.g., cyclandelate, hydralazine, isoxsuprine, minoxidil, nicotynyl, nylidrin, or papaverine), angiotensin converting enzyme inhibitors (e.g., benazepril, captopril, cilazapril, enalapril, enalaprilat, fosinopril, lisinopril, moexipril, perindopril, quinapril, ramipril, or trandolapril), angiotensin II receptor blockers (e.g., candesartan, eprosartan, irbesarten, losartin, telmisartan, or valsartan), alpha blockers (e.g., doxazosin, prazosin, or terazosin) or calcium channel blockers (e.g., amlodipine, bepridil, diltiazem, felodipine, flunarizine, isradipine, mibefradil, nicardipine, nifedipine, nimodipine, nisoldipine, or verapamil). If needed, the second therapeutic agent may be nitroprusside or diazoxide. In addition to a second therapeutic agent, administration of the agent that reduces the level or activity of M-RIP may also be complemented by a low-fat diet, low sodium diet, stress management, physical exercise, reduction in alcohol intake, or reduction in smoking.

The invention also provides a kit containing (a) a therapeutic agent that decreases the level or activity of M-RIP; and (b) instructions for delivery of the agent to a mammal under conditions suitable for treating, reducing, or preventing hypertension or a hypertensive condition. For example, the agent may reduce binding of M-RIP to myosin phosphatase, RhoA, or both.

As used herein, by "M-RIP" is meant a polypeptide that forms a complex with myosin phosphatase and RhoA proteins and therefore regulates myosin phosphatase activity. M-RIP proteins of the invention are substantially identical to the naturally occurring M-RIP of SEQ ID NO: 1. Preferably, the M-RIP decreases myosin phosphatase activity by at least 5%, 10%, 20%, 30%, 40%, 50%, 60%, 70%, 80%, 90%, or more than 100% below control levels as measured by any standard method. Alternatively, the M-RIP protein of the invention may decrease vascular relaxation by at least 5%, 10%, 20%, 30%, 40%, 50%, 60%, 70%, 80%, 90%, or more than 100% below untreated control levels by measuring contractile and relaxant responses in vascular rings, for example, as described by Zhu et al. (*Science* (2002) 5554: 505–8). The activity of the M-RIP protein may also be determined by its ability to increase blood pressure by at least 5%, 10%, 20%, 30%, 40%, 50%, 60%, 70%, 80%, 90%, or more than 100%, as measured by any standard technique.

By an "M-RIP gene" is meant a nucleic acid that encodes an M-RIP protein.

By "substantially identical," when referring to a protein or polypeptide, is meant a protein or polypeptide exhibiting at least 75%, but preferably 85%, more preferably 90%, most preferably 95%, or even 99% identity to a reference amino acid sequence. For proteins or polypeptides, the length of comparison sequences will generally be at least 20 amino acids, preferably at least 30 amino acids, more preferably at least 40 amino acids, and most preferably 50 amino acids or the full length protein or polypeptide. Nucleic acids that encode such "substantially identical" proteins or polypeptides constitute an example of "substantially identical" nucleic acids; it is recognized that the nucleic acids include any sequence, due to the degeneracy of the genetic code, that encodes those proteins or polypeptides. In addition, a "substantially identical" nucleic acid sequence also includes a polynucleotide that hybridizes to a reference nucleic acid molecule under high stringency conditions.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65 C, or a buffer containing 48% formamide, 4.8×SSC, 0.2 M Tris-Cl, pH 7.6, 1× Denhardt's solution, 10% dextran sulfate, and 0.1% SDS, at a temperature of 42 C. Other conditions for high stringency hybridization, such as for PCR, Northern, Southern, or in situ hybridization, DNA sequencing, etc., are well known by those skilled in the art of molecular biology. See, e.g., F. Ausubel et al., *Current Protocols in Molecular Biology*, John Wiley & Sons, New York, N.Y., 1998, hereby incorporated by reference.

By "substantially pure" is meant a nucleic acid, polypeptide, or other molecule that has been separated from the components that naturally accompany it. Typically, the polypeptide is substantially pure when it is at least 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

The term "isolated DNA" is meant DNA that is free of the genes which, in the naturally occurring genome of the organism from which the given DNA is derived, flank the DNA. Thus, the term "isolated DNA" encompasses, for example, cDNA, cloned genomic DNA, and synthetic DNA.

By "M-RIP fusion gene" is meant an M-RIP promoter and/or all or part of an M-RIP coding region operably linked to a second, heterologous nucleic acid sequence. In preferred embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and β-galactosidase.

By "hypertensive condition" is meant any pathological condition resulting from hypertension, or an elevated blood pressure in a mammal. Such conditions are typically cardiovascular, cerebrovascular, or renal.

A mammal is considered to have hypertension if their blood pressure is found to be consistently elevated over optimal levels, or alternatively as having a systolic blood pressure/diastolic blood pressure above 120/80 mmHg. For example, individuals having a systolic pressure of 140 mmHg are amenable to treatment according to the present invention. Mammals diagnosed with hypertension need not have a hypertensive condition to be treated according to this invention.

By "cardiovascular condition" is meant any pathological condition resulting in an injury to the heart, any related cardiac tissue, or the cardiovascular system as a result of hypertension. Such conditions include, for example, vascular injury, blood vessel spasm, myocardial ischemia, angina pectoris, cardiac hypertrophy, myocardial infarct, or congenital heart failure.

By "reduce the level or activity of M-RIP" is meant to reduce the level or biological activity of M-RIP relative to the level or biological activity of M-RIP in an untreated control. According to this invention, such level or activity is reduced by at least 10%, 20%, 30%, 40%, 50%, 60%, 70%, 80%, 90%, 100%, or even greater than 100%, relative to an untreated control. For example, the biological activity of M-RIP is reduced if binding of M-RIP to myosin phosphatase, RhoA, or both is reduced, thereby resulting in a reduction in vascular hypertension.

By "treating, reducing, or preventing hypertension" is meant decreasing the average blood pressure over time in a mammal that has been diagnosed or is at risk of hypertension. For example, mammals having a blood pressure consistently elevated over 140 systolic or 90 diastolic are treated according to the methods of this invention. Such reduction or degree of prevention of hypertension is a reduction in the systolic or diastolic or both of at least 5%, 10%, 20%, 40%, 50%, 60%, 70%, 80%. 90%, or 100% relative to an untreated control as measured by any standard technique.

By "treating, reducing, or preventing a hypertensive condition" is meant ameliorating such condition before or after it has occurred. As compared with an equivalent untreated control, such reduction or degree of prevention is at least 5%, 10%, 20%, 40%, 50%, 60%, 80%, 90%, 95%, or 100% as measured by any standard technique. A patient who is being treated for a hypertensive condition is one who a medical practitioner has diagnosed as having such a condition. Diagnosis may be by any suitable means. Methods for diagnosing vascular damage, such as atherosclerosis, by measuring systemic inflammatory markers are described, for example, in U.S. Pat. Ser. No. 6,040,147, hereby incorporated by reference. Diagnosis and monitoring may also employ urine tests; microscopic urinalysis; hematocrit; measurements of blood levels of serum potassium, serum creatinine, blood urea nitrogen, fasting glucose, thyroid stimulating hormone, lipid content (HDL, LDL, cholesterol and TG), serum calcium, and serum phosphate, or total cholesterol; electrocardiogram, echocardiogram, white blood cell count, or chest X-ray. A patient in whom the development of a hypertensive condition is being prevented may or may not have received such a diagnosis. One in the art will understand that these patients may have been subjected to the same standard tests as described above (electrocardiogram, chest X-ray, etc.) or may have been identified, without examination, as one at high risk due to the presence of one or more risk factors (e.g., family history, hypertension, diabetes mellitus, high cholesterol levels, or having a pathological condition predisposing to secondary hypertension).

By "an effective amount" is meant an amount of a compound, alone or in a combination, required to reduce or prevent hypertension or to treat or prevent a hypertensive condition in a mammal. The effective amount of active compound(s) varies depending upon the route of administration, age, body weight, and general health of the subject. Ultimately, the attending physician or veterinarian will decide the appropriate amount and dosage regimen.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof. For example, a useful candidate compound according to the present invention reduces binding of M-RIP to myosin phosphatase, RhoA, or both.

The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20$^{th}$ edition, (ed. A R Gennaro), Mack Publishing Co., Easton, Pa., 2000.

The present invention provides significant advantages over standard therapies for treatment and prevention of hypertensive conditions resulting from hypertension. Administration of the therapeutic agent that reduces the level or activity of M-RIP according to the present invention attenuates myosin phosphatase activity, in turn causing blood vessel relaxation and lowering blood pressure. In addition, the candidate compound screening methods provided by this invention allow for the identification of novel therapeutics that modify the injury process, rather than merely mitigating the symptoms.

BRIEF DESCRIPTION OF DRAWINGS

FIG. 1A is a schematic diagram showing the amino acid sequence of M-RIP. The human M-RIP sequence (SEQ ID NO: 1) is shown aligned with murine p116RIP3 (SEQ ID NO: 2). The amino acid sequence shared by both sequences is also shown (SEQ ID NO.: 20).

FIG. 1C is a schematic diagram showing the nucleic acid sequence of M-RIP (SEQ ID NO: 19).

Equal proportions of the soluble supernatant and insoluble pellet, as well as an M-RIP immunoprecipitate from the supernatant fraction, were separated by SDS-PAGE, after which M-RIP expression was determined.

Figure 2B:
FIGS. 2A and 2B show a series of immunoblots representing the expression of M-RIP in COS-7 cells (untransfected control (−) or transfected with recombinant M-RIP), in cultured aortic smooth muscle cells (AoSMC), and coronary artery smooth muscle cells (CaSMC).
Figure 2A:
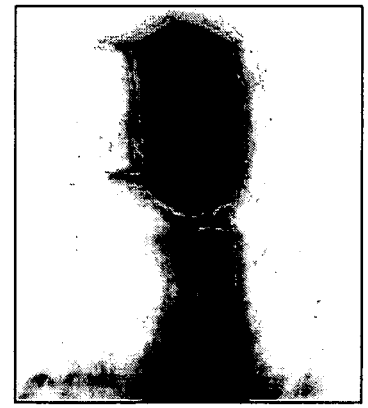
Figure 2C:
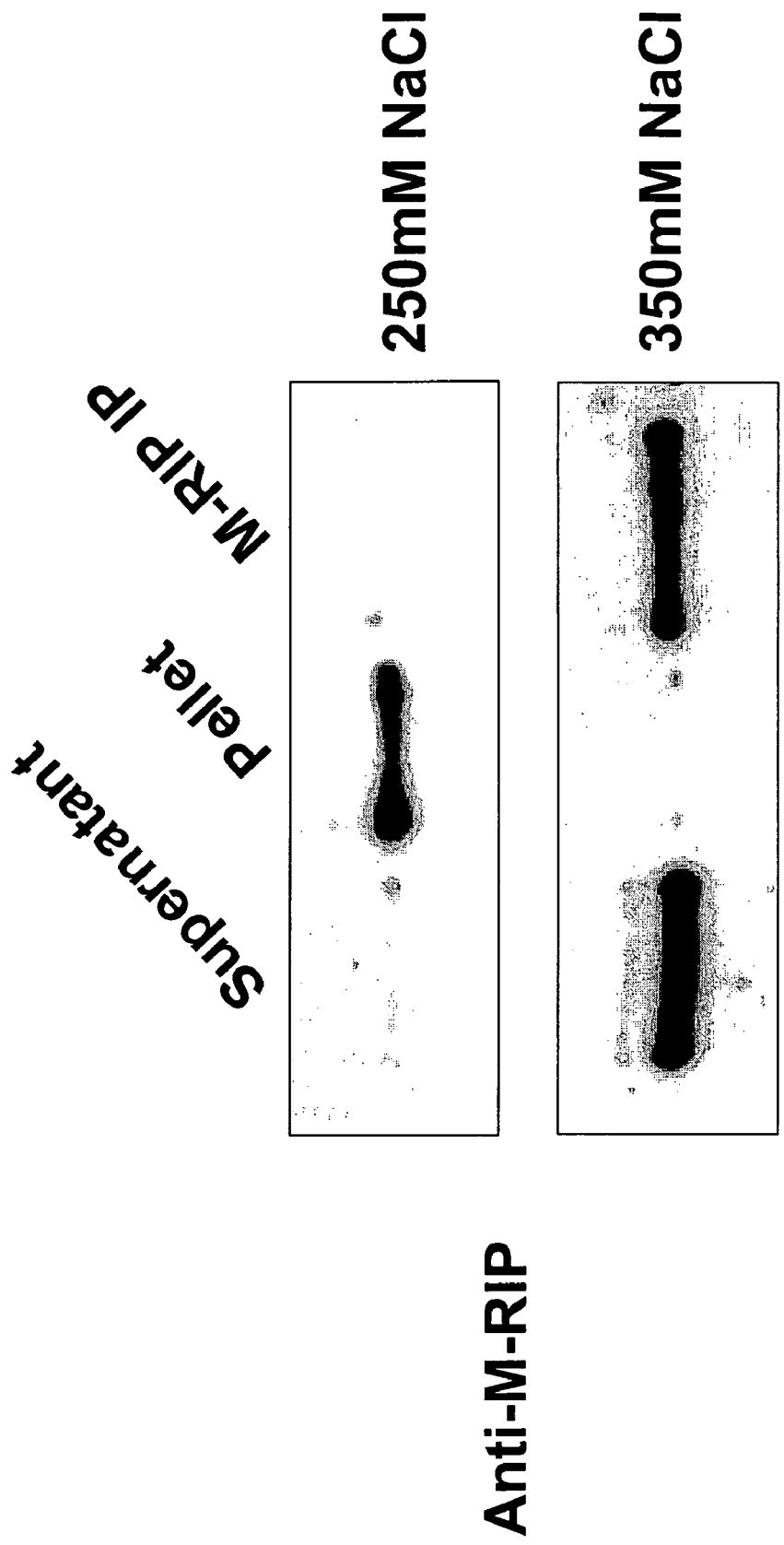
FIG. 2C shows a series of immunoblots representing M-RIP solubility. Aortic smooth muscle cells were lysed in buffer containing 250 or 350 mM NaCl.
Figure 2D:
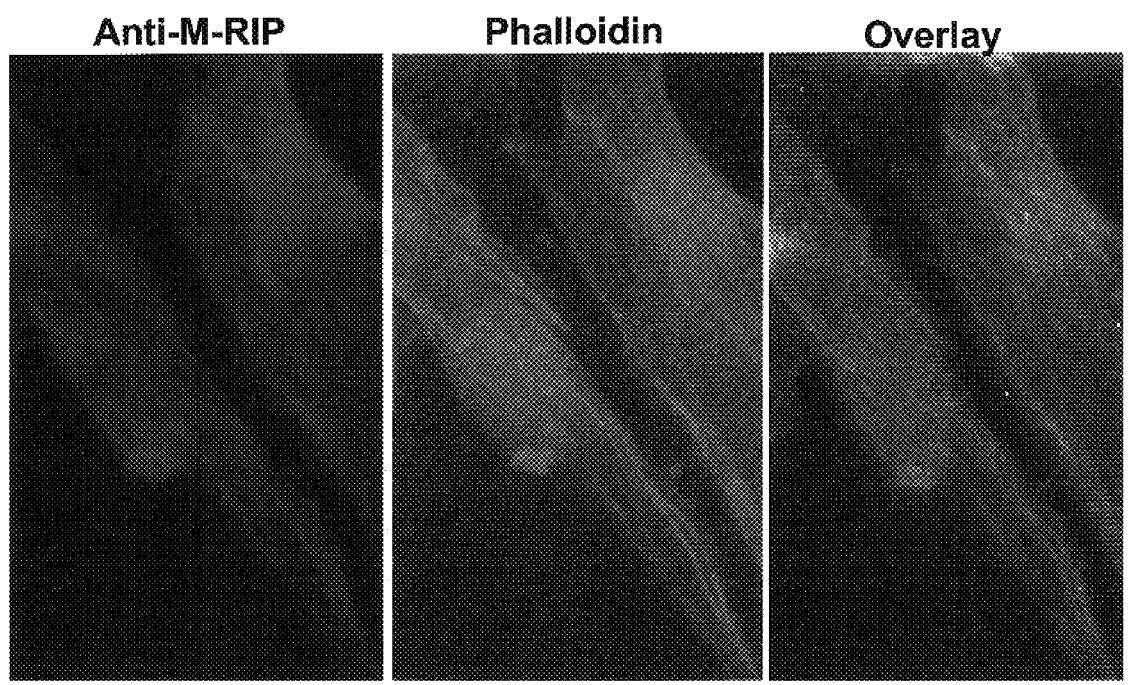

FIG. 2D shows a series of photographs representing coronary artery smooth muscle cells immunostained with anti-MRIP-Cy3 (left panel) and phalloidin-FITC (middle panel). An overlay of the M-RIP and phalloidin immunostained cells is shown in the right panel.

Figure 3A:
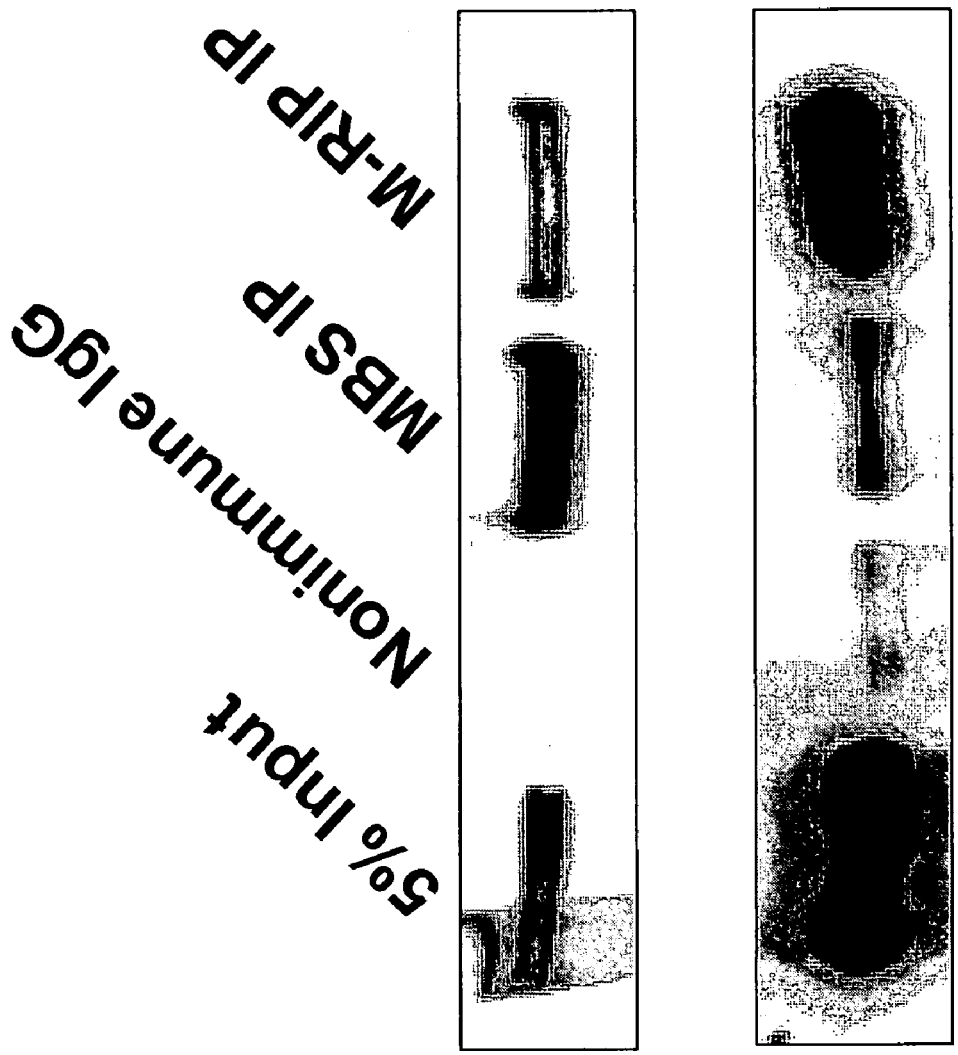

FIG. 3A shows a series of immunoblots representing co-immunoprecipitation experiments to detect the in vivo interaction between M-RIP and myosin phosphatase.

Figure 3B:
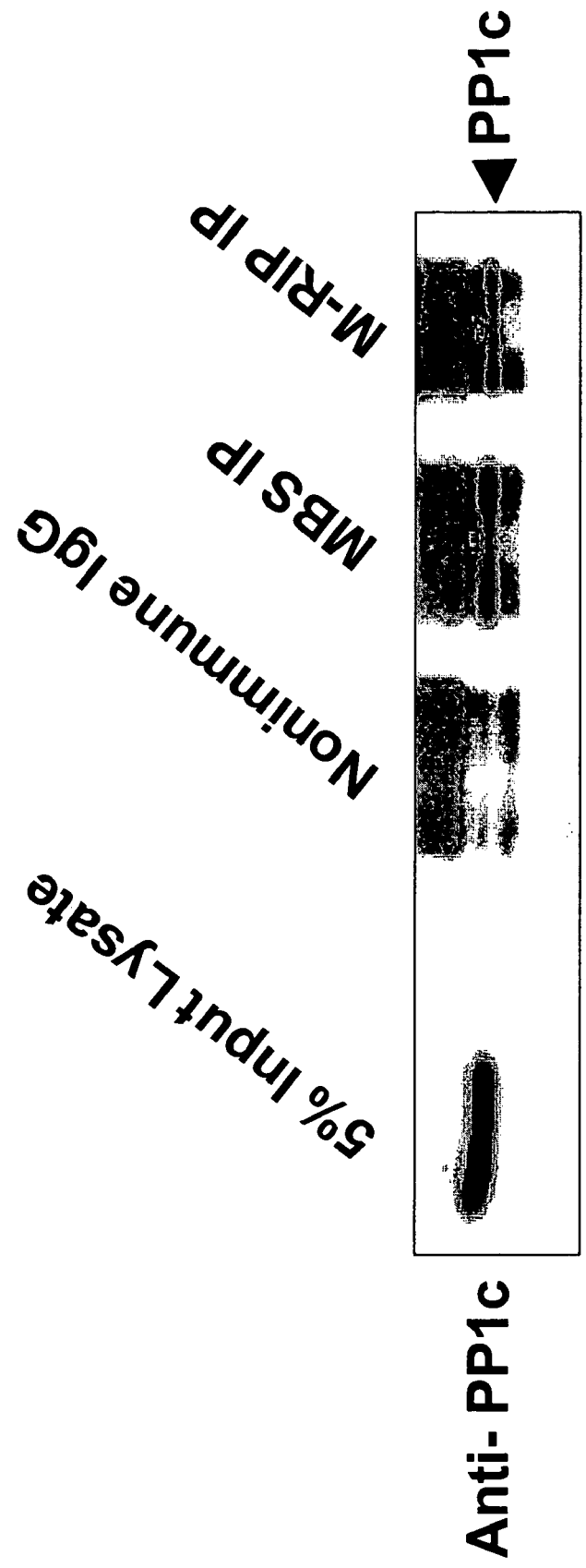

FIG. 3B shows an immunoblot representing a co-immunoprecipitation experiment to detect the in vivo interaction between M-RIP and PP1 in vascular smooth muscle cells.

Figure 3C:
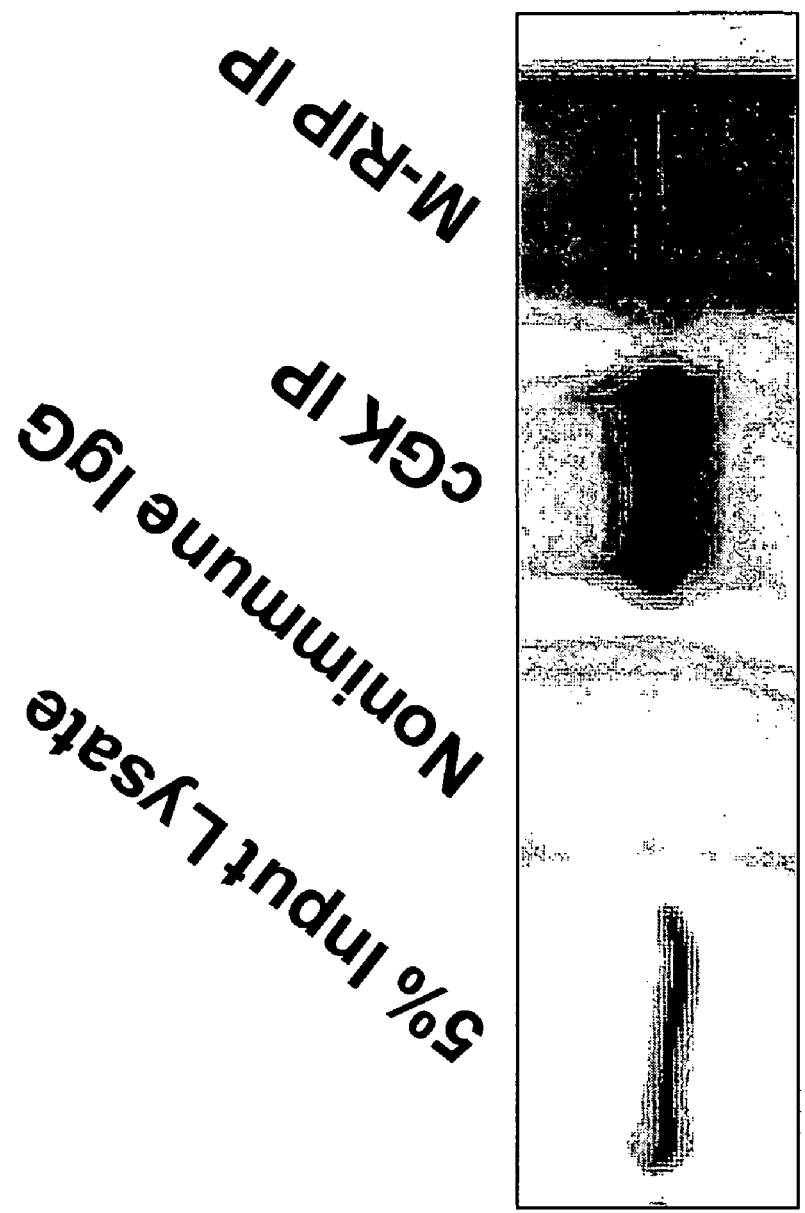

FIG. 3C shows an immunoblot representing a co-immunoprecipitation experiment to detect the in vivo interaction between M-RIP and cGMP-dependent protein kinase (cGK) in vascular smooth muscle cells.

Figure 4A:
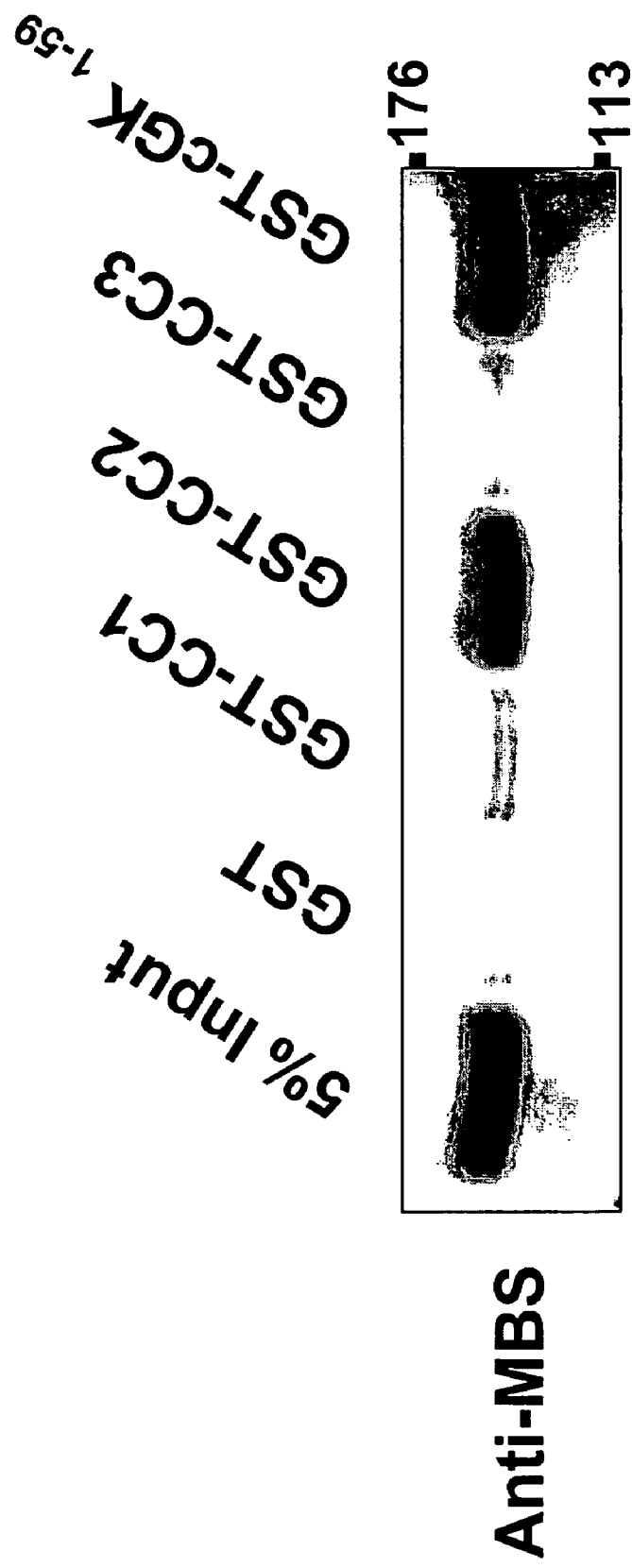

FIG. 4A is an immunoblot to detect binding between M-RIP and myosin phosphatase. Similar quantities of GST fusions of the three coiled coil-domains of M-RIP (CC1, CC2 and CC3) and the amino terminal leucine/isoleucine zipper domain of cGMP-dependent protein kinase 1α were incubated with vascular smooth muscle cell lysate and probed for MBS binding. Molecular weight size markers in kD are shown on the right, and 5% of input lysate is shown on the left.

Figure 4B:
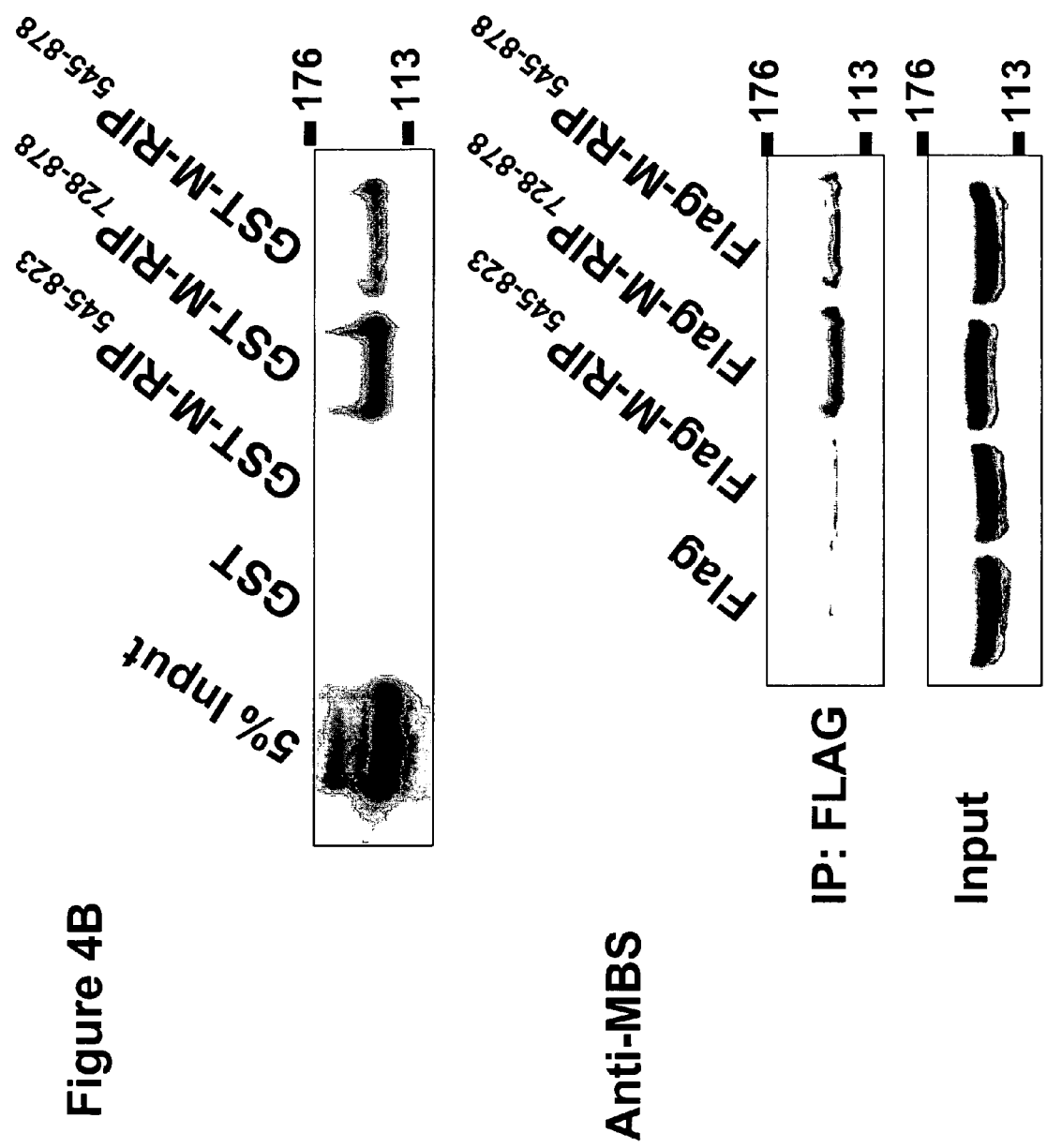

FIG. 4B is a series of immunoblots detecting binding between M-RIP and myosin phosphatase. Similar quantities of GST-fusion proteins of the M-RIP Rho-binding domain (GST-M-RIP545-823), CC2 domain (GST-M-RIP728-878), and Rho-binding domain extended to include the C-terminal CC2 domain (GST-M-RIP545-878) were incubated with vascular smooth muscle cell lysate and immunoblotted for MBS. The upper panel shows the anti-MBS immunoblot. Also shown is the same M-RIP domains expressed in COS1 cells as Flag-tagged proteins and immunoprecipitated with M2 antibody. The MBS immunoblot of the immunopellets is shown in the middle panel and the total cellular MBS content from each lysate used for immunoprecipitation is shown in the lower panel. Molecular weight size markers in kD are shown on the right.

FIG. 4C is a schematic diagram showing domains of M-RIP tested for MBS binding with the corresponding amino acid numbers. The hatched box represents the Rho-binding domain. MBS binding to each domain is shown by a (−) or (+) on the right.

Figure 4D:
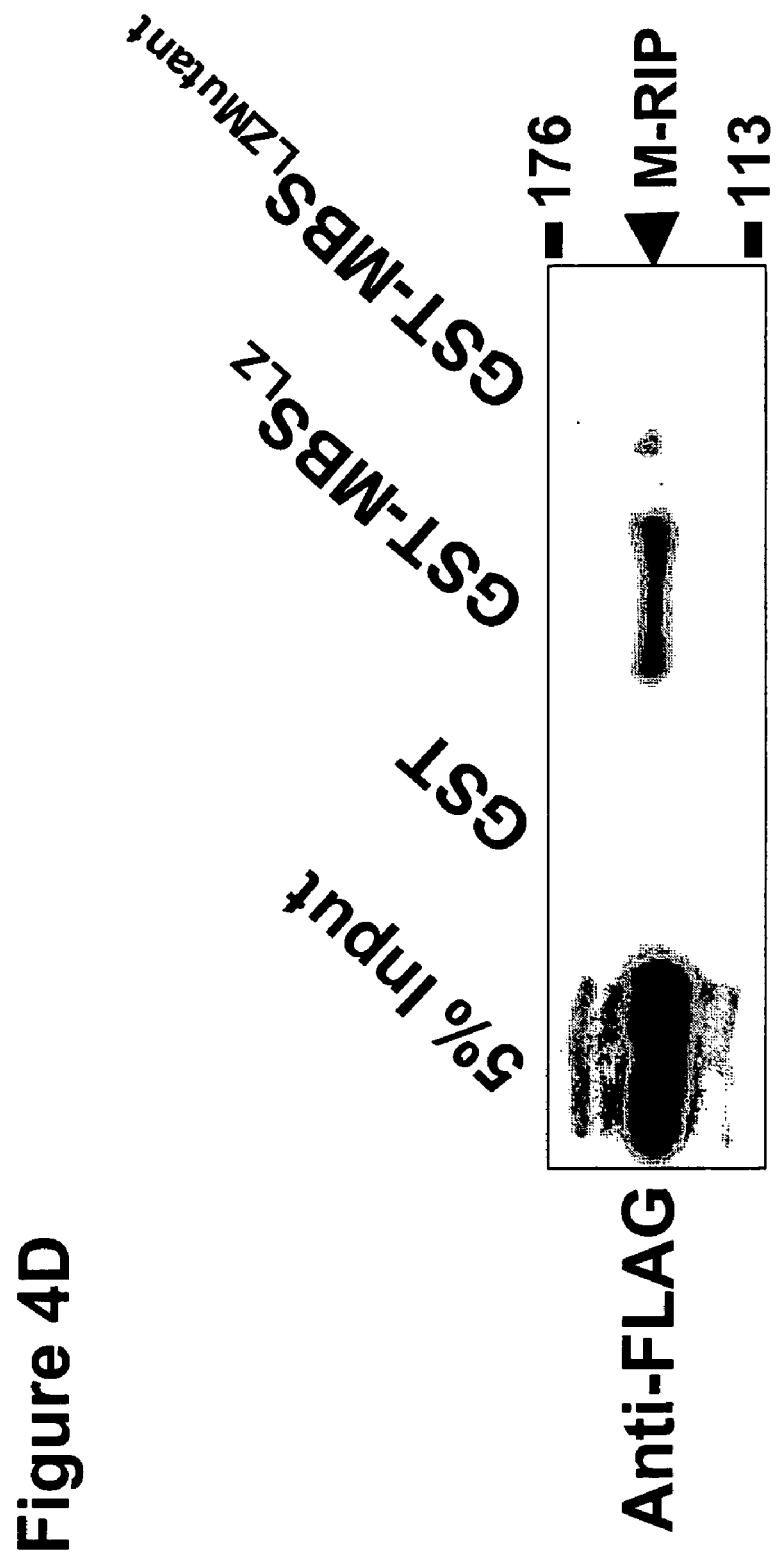

FIG. 4D shows an immublot representing the C-terminal 180 amino acids of MBS which includes the leucine zipper domain (GST-MBSLZ) or in which all four leucines in the leucine zipper were mutated to alanines (GST-MBSLZmutant). Following an incubation with COS-7 cell lysate overexpressing flag-tagged MRIP, M-RIP binding was probed to detect binding with anti-Flag (M2). Molecular weight markers are shown on the right, and 5% of input lysate is shown on the left.

Figure 4E:
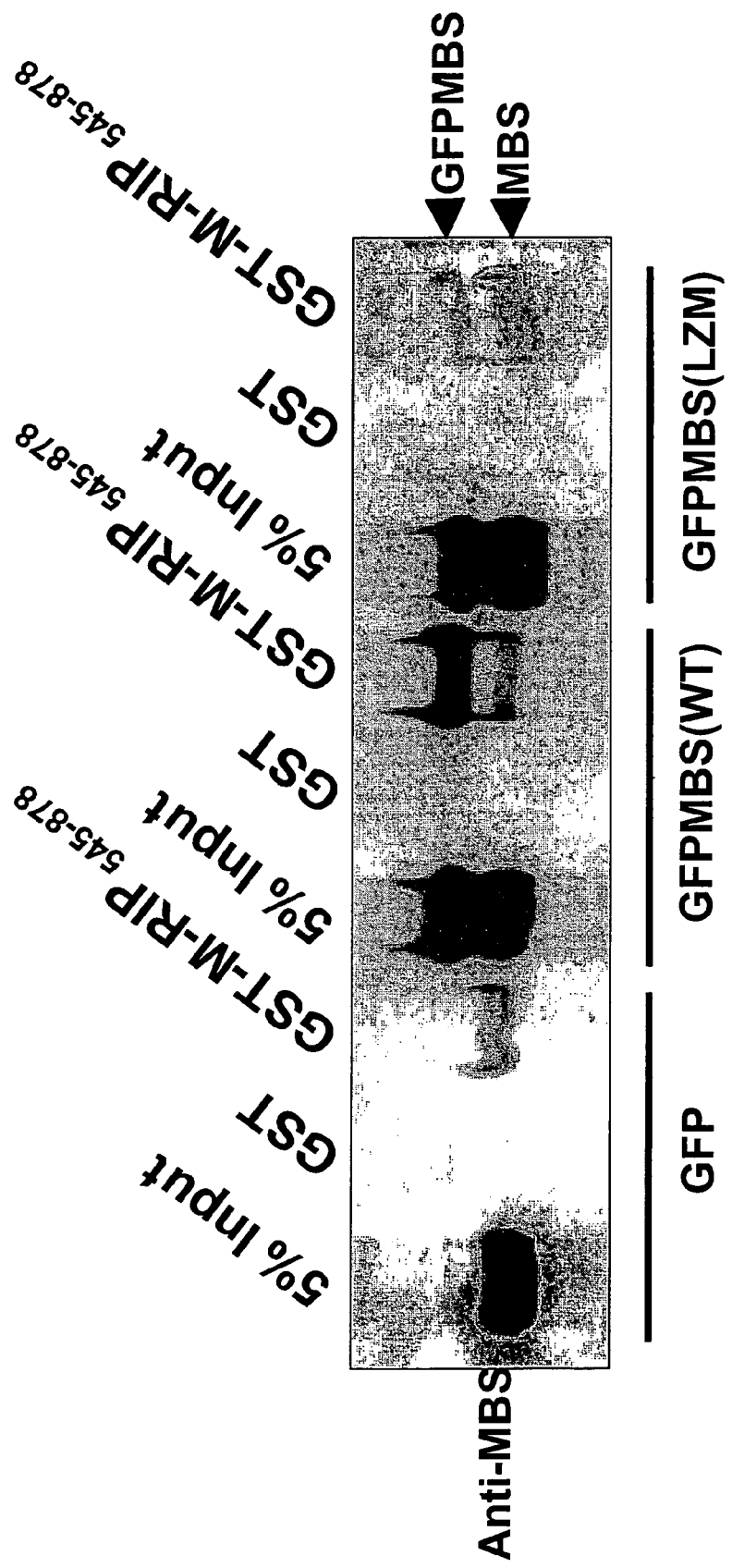

FIG. 4E is an immunoblot showing COS1 cells transfected with GFP, GFPMBS, or GFPMBSLZM. Cells were lysed and incubated with GST or GST-M-RIP545-878. Bound MBS, GFPMBS, and GFPMBSLZM were detected with anti-MBS antibodies. The positions of MBS and GFP-MBS are shown by the arrowheads on the right.

Figure 4F:
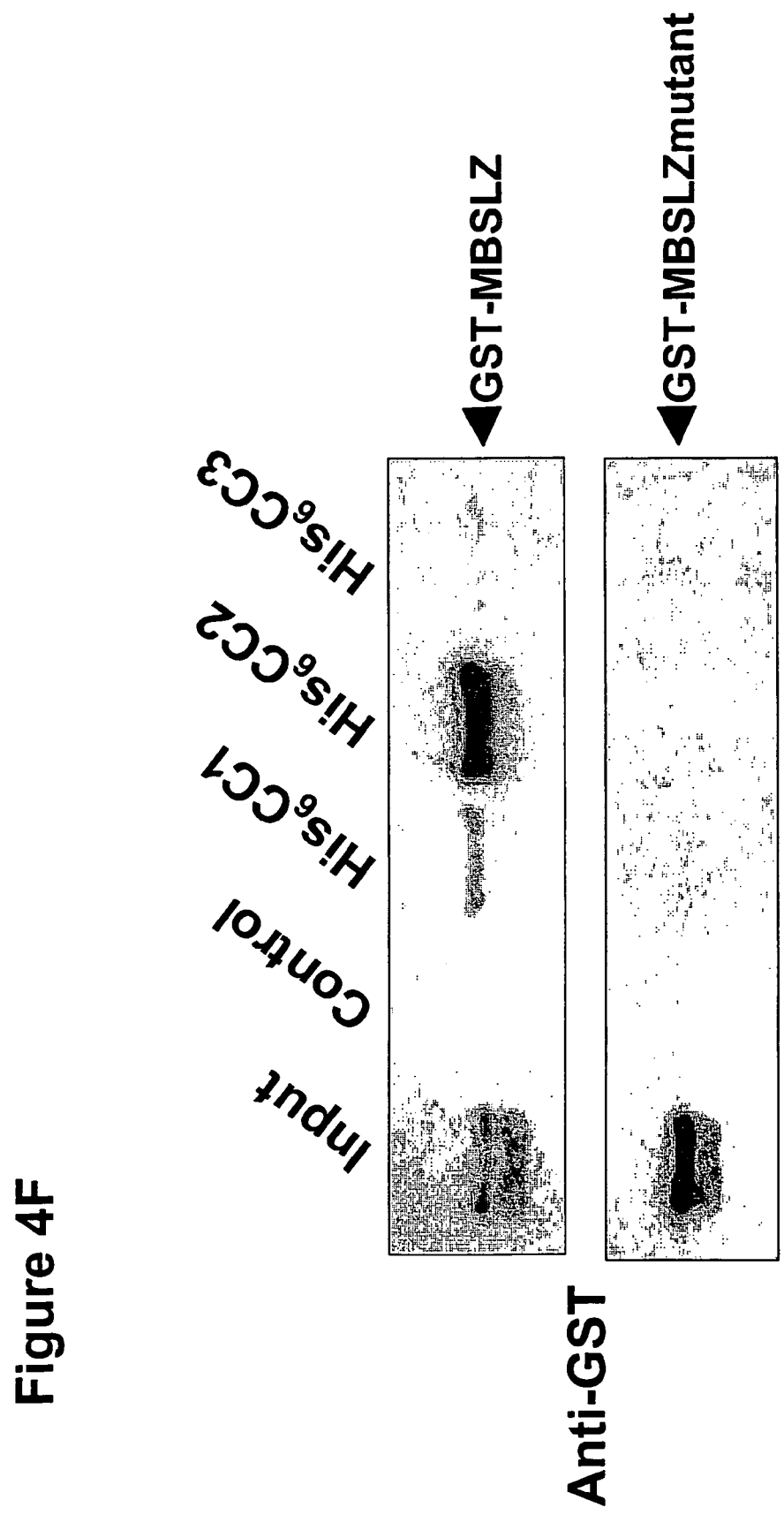

FIG. 4F show a series of immunoblots representing a purified protein interaction assay in which similar quantities of 6×his CC1, CC2, and CC3 bound to Ni-NTA beads were incubated with purified soluble GST-MBSLZ or GST-MBSLZ mutant. Bound GST-MBSLZ and GST-MBSLZ mutant were detected using anti-GST antibodies.

Figure 5A:
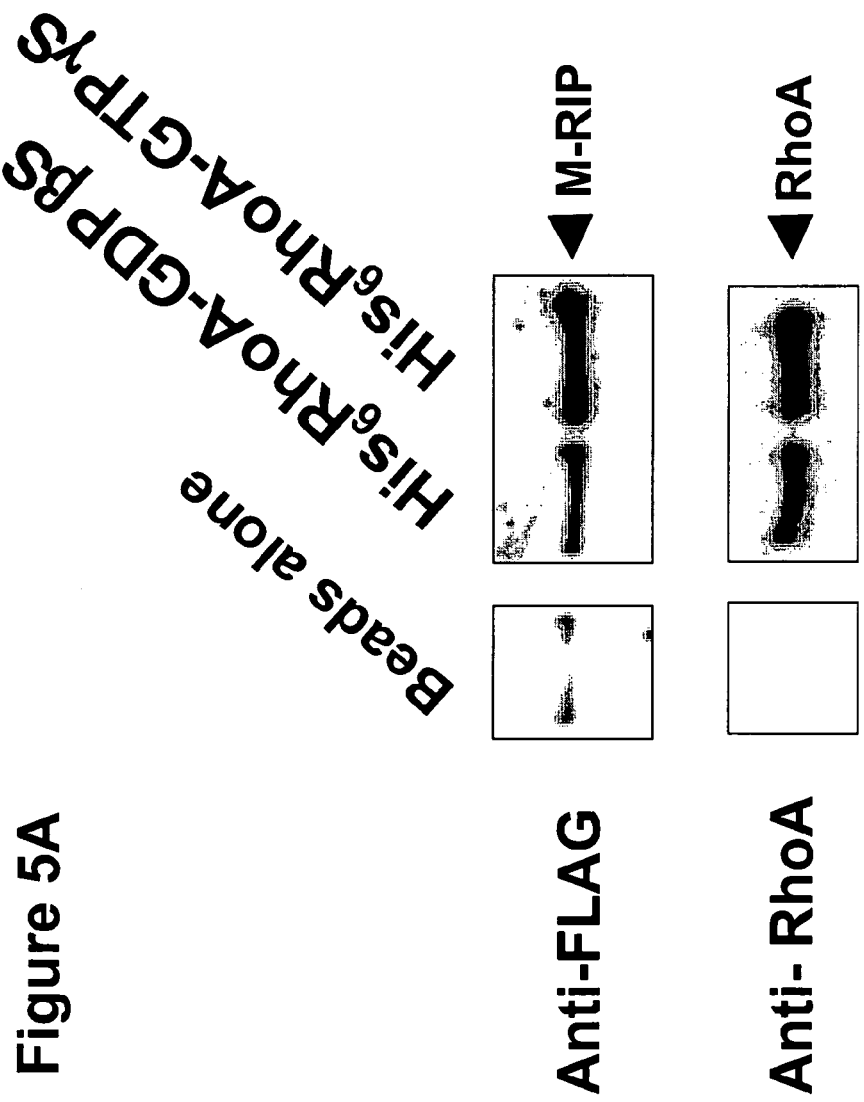

FIG. 5A is a series of immunoblots. Purified, recombinant 6×his RhoA was loaded with GDPβS or GTPγS, incubated with COS1 lysate containing overexpressed Flag M-RIP, and precipitated with Ni-NTA beads. As a negative control, lysate incubated with beads but without any added 6×his-RhoA is shown on the left. The top panel shows bound M-RIP detected using anti-Flag (M2). Differences in M-RIP binding were not significant (P=NS). The bottom panel shows input 6×his RhoA, detected by anti-RhoA antibody.

Figure 5B:

FIG. 5B is an immunoblot representing a purified protein interaction study in which 6×his RhoA loaded with GDPβS or GTPγS was incubated with GST, GST-RhotekinRBD, GST-M-RIP545-823, and GST-MRIP545-878 bound to glutathione-agarose beads. Bound 6×his RhoA was detected using anti-RhoA antibodies. Amounts of input GST-fusion proteins were equivalent as detected by Ponceau stain (DNS).

Figure 5C:
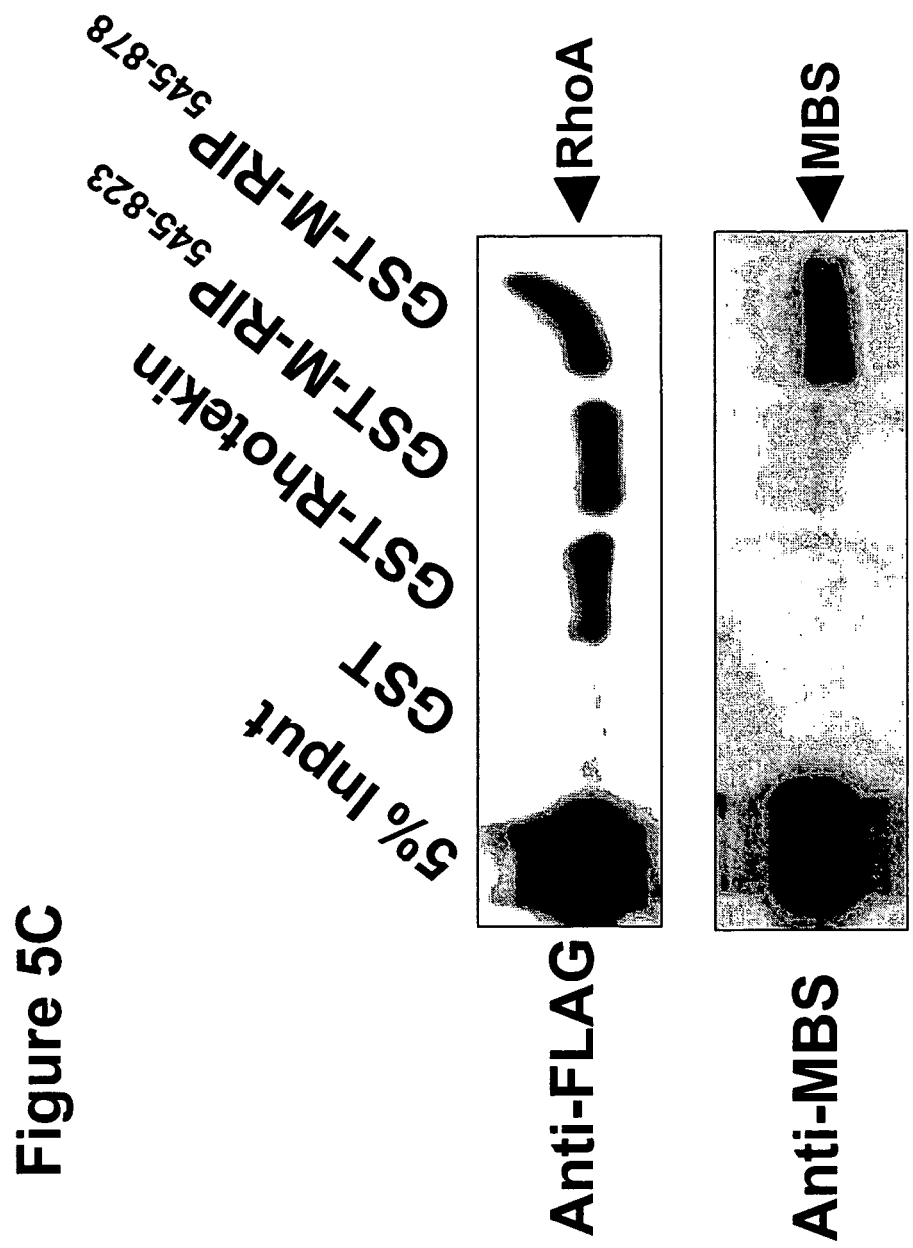

FIG. 5C shows a series of immunoblots. COS1 cells transfected with Flag-RhoA were lysed in buffer A and incubated with GST, GST-RhotekinRBD, GST-M-RIP545-823, and GST-M-RIP545-878 bound to glutathione-agarose beads. Aliquots of the bound protein were separated on 12.5% and 7.5% protein gels and immunoblots for Flag (M2) and MBS were performed, respectively. 5% of input lysate is shown on the left.

Figure 6A:
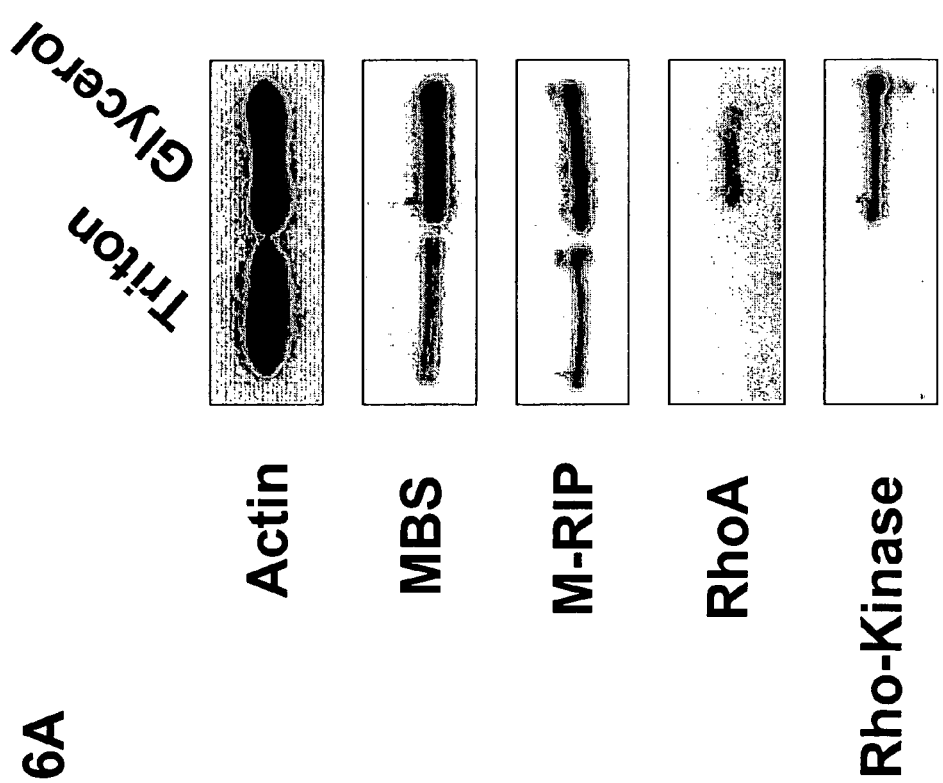

FIG. 6A is a series of immunoblots demonstrating that M-RIP is associated with RhoA/Rho-kinase in vivo. Stress fibers isolated by Triton extraction (left column) or glycerol extraction (right column) of aortic smooth muscle cells and immunoblotted with anti-actin, anti-MBS, anti-M-RIP, anti-RhoA, and anti-Rho-Kinase.

FIG. 6B is a series of immunostains of human coronary artery myocytes extracted with glycerol and double labeled with phalloidin (left panels) and the indicated antibodies (right panels).

Figure 6C:
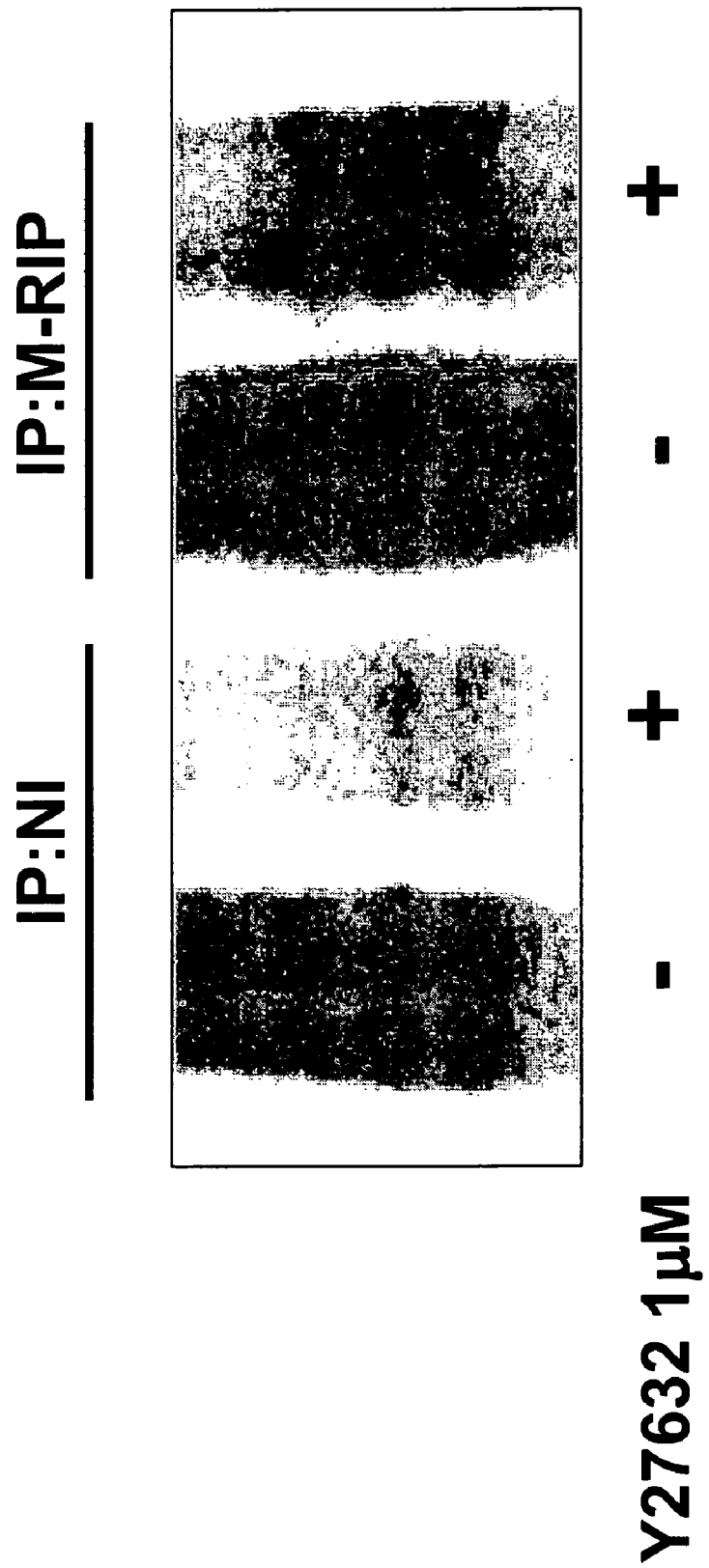

FIG. 6C is an immunoblot demonstrating kinase activity in nonimmune and M-RIP immunopellets from aortic smooth muscle cells incubated without (−) and with (+) the Rho-Kinase inhibitor Y27632. Shown is the Autoradiogram of the samples separated by SDS-PAGE.

FIG. 6D is a graph showing densitometry of the two dominant bands in the M-RIP immunopellet without (−) and with (+) Y27632.

Figure 7:
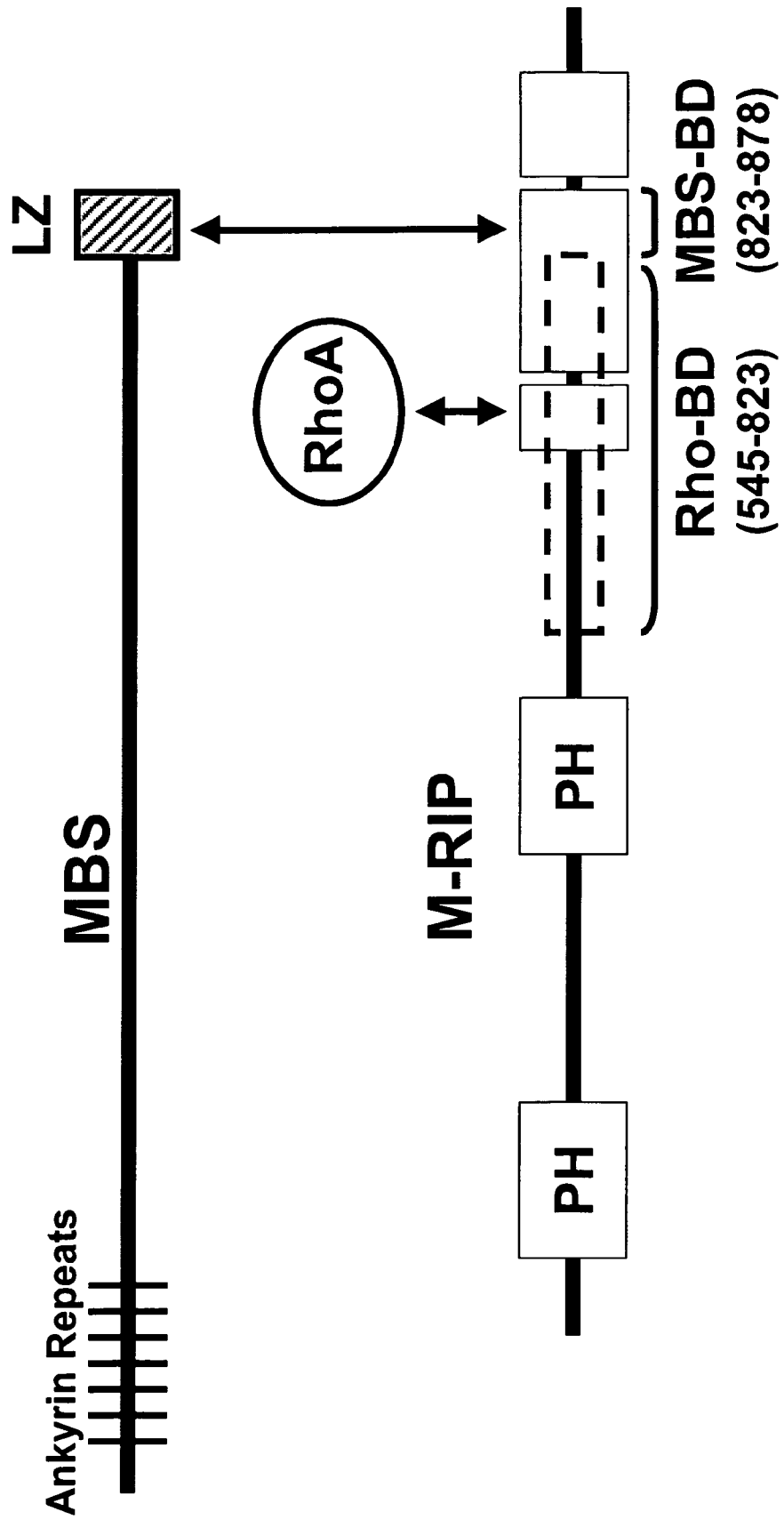

FIG. 7 is a schematic diagram showing a model of M-RIP interactions with RhoA and MBS. Direct binding interactions are shown by arrows. "LZ" designates leucine zipper, "MBS-BD" designates MBS-binding domain, "Rho-BD" designates Rho-binding domain, and "PH" designates pleckstrin homology domain. The hatched square depicts the Rho-binding domain. Amino acid numbers for the interacting domains are shown in parenthesis.

DETAILED DESCRIPTION

Normal blood pressure is maintained by chemical and rheologic stimuli, which control vascular smooth muscle cell tone in a complex and dynamic fashion. Blood vessel tone is regulated by the contractile state of vascular smooth muscle cells in the blood vessel wall. Diseases characterized by abnormal vascular smooth muscle cell contraction include hypertension, blood vessel spasm, and atherosclerosis. Hypertension, an elevation of arterial blood pressure, poses a serious health risk in developed countries. If untreated, hypertension often results in serious secondary complications, including various forms of cardiovascular, cerebrovascular, and renal disorders. Currently, therapeutic modalities to reduce elevated blood pressure are somewhat limiting and are sometimes associated with debilitating side effects. Thus, better methods for the treatment and prevention of hypertension and hypertensive conditions are desirable. The present invention fulfills this need by providing such methods.

The Role of Smooth Muscle Cell Contraction and Relaxation in Hypertension: Molecular Mechanisms Smooth muscle contraction is tightly coupled to myosin light chain phosphorylation, which in turn is regulated by the relative activities of myosin light chain kinase and myosin phosphatase. Myosin light chain kinase is activated by intracellular calcium and phosphorylates myosin light chains, leading to cell contraction. Myosin phosphatase dephosphorylates myosin light chains, leading to smooth muscle cell relaxation.

Myosin phosphatase activity, once thought to be constitutive, is now known to be highly regulated. While vasoconstrictor signaling pathways result in the inhibition of myosin phosphatase and cell contraction, vasodilator signaling pathways result in cell relaxation following the activation of myosin phosphatase. G-protein coupled receptor agonists inhibit myosin phosphatase by activating RhoA/Rho-kinase and NO/cGMP activates myosin phosphatase causing smooth muscle cell relaxation subsequent to cGMP-dependent protein kinase activation.

Myosin phosphatase is a heterotrimer containing a PP1 catalytic subunit, a 130 kD myosin binding subunit (MBS), and a 20 kD subunit of unknown function. The MBS is a regulatory subunit that targets PP1 to its substrate, myosin light chain and that has multiple protein interaction domains, including ankyrin repeats at its amino terminus and a leucine zipper domain at its carboxy terminus. MBS binds PP1 and myosin light chain at its amino terminus and the M20 subunit and cGMP-dependent protein kinase 1α(cGK) at its carboxy-terminus. The MBS-cGK interaction is necessary for NO/cGMP-mediated activation of myosin phosphatase. In vascular smooth muscle, G-protein coupled receptor agonists cause contraction in part by inhibition of myosin phosphatase activity. Several downstream signaling pathways that inhibit myosin phosphatase activity have been discovered recently, including RhoA/Rho-kinase, protein kinase C activation of the inhibitory phosphoprotein CPI-17, and arachidonic acid. In addition, several kinases co-purify with myosin phosphatase, including ZIP-like kinase, integrin-linked kinase, myotonic dystrophy related kinase, and Raf-1, each of which can phosphorylate MBS and inhibit myosin phosphatase activity. RhoA/Rho-kinase has been the most extensively studied myosin phosphatase inhibitor. RhoA binds to a myosin phosphatase complex in vitro, and GTP-bound RhoA, in combination with its downstream effector Rho-kinase, inhibits myosin phosphatase activity. Specific blockade of Rho-kinase can ameliorate hypertension in several rat models, as well as to prevent the response to vascular injury and blood vessel spasm in animal models. Furthermore, phosphorylation-specific antibodies against inhibitory sites on MBS demonstrate that phosphorylation correlates directly with contractile agonist-mediated myosin phosphatase inhibition. Rho kinase inhibitors are also effective in preventing coronary artery spasm and treating myocardial ischemia in humans.

Despite the strong evidence for RhoA/Rho-kinase-mediated inhibition of myosin phosphatase, the molecular mechanism for this contractile pathway is not well understood. Activated RhoA and Rho-kinase translocate to the cell membrane and have also been found colocalized with actin myofilaments. The mechanism whereby RhoA and Rho-kinase are targeted to and inhibit myosin phosphatase and thereby prevent dephosphorylation of myosin light chains in contractile myofilaments, remains unclear.

Identification of M-RIP

The present invention involves the discovery of myosin phosphatase-Rho interacting protein (M-RIP) and the fact that this protein forms a complex with myosin phosphatase and RhoA, thereby leading to a reduction in myosin phosphatase activity and ultimately resulting in vascular smooth muscle cell contraction and hypertension. Accordingly, the invention provides methods for screening candidate compounds for those that are useful for the treatment, reduction, or prevention of hypertension, hypertensive conditions, or both. Based on our studies, the administration of an agent that reduces the activity or level of M-RIP (e.g., by reducing binding of M-RIP to myosin phosphatase or RhoA) results in the treatment, prevention, or reduction of hypertension in a mammal.

Using a yeast-two hybrid screen, we have identified M-RIP, a 116 kD human protein that is highly homologous to murine p116RIP3 and that interacts with both myosin phosphatase and RhoA. M-RIP is expressed in vascular smooth muscle and is localized to actin myofilaments. M-RIP binds directly to the myosin binding subunit (MBS) of myosin phosphatase in vivo in vascular smooth muscle cells by virtue of coiled-coil and leucine zipper domains present within the two proteins. In addition, an adjacent domain of M-RIP directly binds RhoA in a nucleotide-independent manner. Our studies show that M-RIP copurifies with RhoA and Rho-kinase, colocalizes on actin stress fibers with RhoA and MBS, and is associated with Rho-kinase activity in vascular smooth muscle cells. Our results showing that m-RIP assembles in a complex containing both RhoA and MBS indicate that M-RIP plays a role in myosin phosphatase regulation by RhoA. Our results therefore indicate that M-RIP binds myosin phosphatase, and RhoA in vascular smooth muscle cells, thus forming a complex localized to actin myofilaments. In this manner, M-RIP may target RhoA to the myosin phophatase complex to inhibit myosin phosphatase. Overall, these data show that M-RIP is a key player in smooth muscle contraction by virtue of its interaction with myosin phosphatase and identify M-RIP as an important regulator of normal vascular tone. Thus, M-RIP represents a useful target for the development of therapies for abnormalities of blood pressure. The administration of a therapeutic agent that reduces the levels or activity of M-RIP decreases smooth muscle cell contraction by increasing the activity of myosin phosphatase. In turn, relaxation of blood vessels is increased such that hypertension or hypertensive conditions are treated, prevented, or reduced in a mammal.

The methods of this invention are particularly useful for the prevention and treatment of conditions resulting from hypertension, which often lead to morbidity if untreated. Such conditions are typically cardiovascular (e.g., cardiac hypertrophy, myocardial infarct, angina pectoris, congestive heart failure, vascular injury, blood vessel spasm, myocardial ischemia, myocardial infarct, or coronary arterial diseases such as atherosclerosis and arteriosclerosis, and aortic dissection) cerebrovascular (e.g., cerebral infarction, cerebral hemorrhage, brain damage, or loss of vision) or renal (e.g., kidney damage or failure).

Screening Assays

The present invention provides screening methods to identify compounds that can inhibit the level or activity of M-RIP. Useful compounds include any agent that inhibits the biological activity or reduces the cellular level of M-RIP. For example, candidate compounds may reduce binding of M-RIP to myosin phosphatase, RhoA, or both. Using such agents as lead compounds, for example, the present screening methods also allow the identification of further novel, specific inhibitors of M-RIP that function to treat, reduce, or prevent hypertension. The method of screening may involve high-throughput techniques.

A number of methods are available for carrying out such screening assays. According to one approach, candidate compounds are added at varying concentrations to the culture medium of cells expressing M-RIP. Gene expression of M-RIP is then measured, for example, by standard Northern blot analysis (Ausubel et al., supra), using any appropriate fragment prepared from the nucleic acid molecule of M-RIP as a hybridization probe or by real time PCR with appropriate primers. The level of gene expression in the presence of the candidate compound is compared to the level measured in a control culture medium lacking the candidate molecule. If desired, the effect of candidate compounds may, in the alternative, be measured at the level of M-RIP polypeptide or myosin phosphatase activity using the same general approach and standard immunological techniques, such as Western blotting or immunoprecipitation with an antibody specific to M-RIP for example. For example, immunoassays may be used to detect or monitor the level of M-RIP. Polyclonal or monoclonal antibodies which are capable of binding to M-RIP may be used in any standard immunoassay format (e.g., ELISA or RIA assay) to measure the levels of M-RIP. M-RIP can also be measured using mass spectroscopy, high performance liquid chromatography, spectrophotometric or fluorometric techniques, or combinations thereof.

Alternatively, the screening methods of the invention may be used to identify candidate compounds that decrease the biological activity of M-RIP by reducing binding of M-RIP to myosin phosphatase, RhoA, or both by at least 10%, 20%, 30%, 40%, 50%, 60%, 70%, 80%, 90%, 95%, or 100% relative to an untreated control. For example, a candidate compound may be tested for its ability to decrease M-RIP activity in cells that naturally express M-RIP, after transfection with cDNA for M-RIP, or in cell-free solutions containing M-RIP, as described further below. The effect of a candidate compound on the binding or activation of M-RIP can be tested by radioactive and non-radiaoctive binding assays, competition assays, and receptor signaling assays.

As a specific example, mammalian cells (e.g., rodent cells) that express a nucleic acid encoding M-RIP are cultured in the presence of a candidate compound (e.g., a peptide, polypeptide, synthetic organic molecule, naturally occurring organic molecule, nucleic acid molecule, or component thereof). Cells may either endogenously express M-RIP or may alternatively be genetically engineered by any standard technique known in the art (e.g., transfection and viral infection) to overexpress M-RIP. The expression level of M-RIP is measured in these cells by means of Western blot analysis and subsequently compared to the level of expression of the same protein in control cells that have not been contacted by the candidate compound. A compound which promotes a decrease in the level of M-RIP activity as a result of reducing its synthesis or biological activity is considered useful in the invention.

In one particular example, a compound that interferes with M-RIP binding to myosin phosphatase, RhoA, or both (thereby reducing the biological activity of M-RIP), leading to a reduction in vascular contraction, is useful according to the present invention. Given its ability to decrease the biological activity of M-RIP, such a molecule may be used, for example, as a therapeutic agent to treat, reduce, or prevent hypertension or a hypertensive condition. As a specific example, a candidate compound may be contacted with two proteins, the first protein being a polypeptide substantially identical to M-RIP (e.g., SEQ ID NO: 1) and the second protein being myosin phosphatase or RhoA (i.e., a protein that binds the M-RIP under conditions that allow binding and that results in vascular smooth muscle cell contraction). According to this particular screening method, the interaction between these two proteins is measured following the addition of a candidate compound. A decrease in the binding M-RIP to the second polypeptide following the addition of the candidate compound (relative to such binding in the absence of the compound) identifies the candidate compound as having the ability to inhibit the interaction between the two proteins, and thereby having the ability to reduce vascular smooth muscle cell contraction. Alternatively, the binding of M-RIP to myosin phosphatase, RhoA, or both may be tested by assaying for the activity of myosin phophatase. Myosin phosphatase activity may be determined by any method known in the art, including for example, partial purification of phoshatase from cell extracts (Verin et al, Am. J.Physiol. 269; Lung (1995) Cell. Mol. Physiol. 13: L99–L108; Essler et al, (1998) J. Biol Chem. 273: 21867–21874) or by immunoprecipitaton of phosphatase from cell extracts (Totsukawa et al, (1999) J. Cell Biol. 144: 735–744). With either method, phosphatase is then mixed with radio-labeled phosphatase substrate, myosin light chain, and the liberated labeled phosphate is measured and is proportional to phosphatase activity. Ultimately, the screening assay of the invention may be carried out, for example, in a cell-free system or using a yeast two-hybrid system. If desired, one of the proteins or the candidate compound may be immobilized on a support as described above or may have a detectable group.

Alternatively, or in addition, candidate compounds may be screened for those which specifically bind to and thereby inhibit M-RIP. The efficacy of such a candidate compound is dependent upon its ability to interact with M-RIP. Such an interaction can be readily assayed using any number of standard binding techniques and functional assays (e.g., those described in Ausubel et al., supra). For example, a candidate compound may be tested in vitro for interaction and binding with M-RIP and its ability to modulate smooth muscle cell contractility may be assayed by any standard assays (e.g., those described herein).

In one particular example, a candidate compound that binds to M-RIP may be identified using a chromatography-based technique. For example, a recombinant M-RIP may be purified by standard techniques from cells engineered to express M-RIP (e.g., those described above) and may be immobilized on a column. Alternatively, the naturally-occurring M-RIP may be immobilized on a column. A solution of candidate compounds is then passed through the column, and a compound specific for M-RIP is identified on the basis of its ability to bind to M-RIP and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography).

Screening for new inhibitors and optimization of lead compounds may be assessed, for example, by assessing myosin phosphatase activity using standard techniques. In addition, these candidate compounds may be tested for their ability to function as anti-hypertensive agents (e.g., as described herein). Compounds isolated by this approach may also be used, for example, as therapeutics to treat, reduce, or prevent hypertension. Compounds which are identified as binding to M-RIP with an affinity constant less than or equal to 10 mM are considered particularly useful in the invention.

Ultimately, the anti-hypertensive efficacy of any of the candidate compounds identified by the present screening methods may be tested using any of the smooth muscle vascular contraction models described herein.

Potential therapeutic agents include organic molecules, peptides, peptide mimetics, polypeptides, and antibodies that bind to a nucleic acid sequence or polypeptide that encodes M-RIP and thereby inhibit or extinguish their activity. Potential anti-hypertensive agents also include small molecules that bind to and occupy the binding site of such polypeptides thereby preventing binding to cellular binding molecules, such that normal biological activity is prevented. Other potential anti-hypertensive agents include antisense molecules.

Test Compounds and Extracts

In general, compounds capable of reducing hypertension are identified from large libraries of both natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, ftingal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-hypertensive activity should be employed whenever possible.

When a crude extract is found to have an anti-hypertensive activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having anti-hypertensive activity. Methods of fractionation and purification of such heterogenous extracts are known in the art. If desired, compounds shown to be useful agents for the treatment of pain are chemically modified according to methods known in the art.

Murine Vascular Rings Studies

Murine Vascular Ring Studies may be used to measure smooth muscle cell contraction and may employ mouse thoracic aortas prepared, equilibrated, and used in isometric tension studies as previously described by Zhu et al. (*Science* (2002) 5554:505–8).

Blood Pressure Measurements

To assess the anti-hypertensive properties of a candidate compound, the candidate compound may be tested for its ability to reduce hypertension in vivo, for example in mice as follows. Prior to surgical procedures, mice (27–33 g) are anesthetized with ketamine/xylazine (87 mg/kg/13 mg/kg ip) and monitored for depth of anesthesia/analgesia on a pre-warmed operating surface. The right common carotid artery is catheterized with a Millar (Houston, Tex.) 1.4 French blood pressure probe with transducer linked to a PowerLab/4SP (ADInstruments, New Castle, NSW, Australia) interface. Mean arterial pressures and heart rates are continuously monitored using the Chart 4.1 Software package (ADInstruments). In the absence of ganglionic blockade or surgical vagotomy mice typically undergo periods of severe bradycardia (180–220 bpm) shortly after administration of ketamine/xylazine anesthesia. Data for mean pressures is, therefore, typically recorded at later experimental time points (>20 minutes postanesthesia) when the heart rates stabilize above 300 bpm. Blood pressure measurements in conscious, freely ambulatory mice were made using implantable, miniaturised mouse blood pressure transmitters (Data Sciences International, St Paul, Minn.) to directly measure mean arterial pressure from within conscious individual animals, as described previously by Zhu et al. (*Science* (2002) 5554:505–8). Typically, transducer sampling frequency is hourly at 500 hfr/sec for five seconds (2500 points per hour).

Pharmaceutical Compositions

According to the present invention, the administration to a mammal of an agent that reduces the level or activity of M-RIP leads to the activation of myosin phosphatase in smooth muscle cells. The consequent decreased contractile and increased relaxation responses in blood vessels ultimately lower the systemic blood pressure of the mammal suffering from hypertension. By decreasing the elevated blood pressure, the administration of the agent of the invention is particularly useful to treat, prevent, or reduce hypertensive conditions.

An inhibitor of M-RIP is any agent having the ability to reduce the level or the activity of M-RIP by at least 10%, 20%, 30%, 40%, 50%, 60%, 70%, 80%, 90%, or 100% relative to an untreated control cell, as determined by any standard method in the art, including those described herein. Optionally, this agent may inhibit or reduce binding of M-RIP to myosin phosphatase, RhoA, or both. Desirably, the agent of the invention treats, prevents, or reduces hypertension or a hypertensive condition when administered to a mammal by at least 10%, 20%, 30%, 40%, 50%, 60%, 70%, 80%, 90%, or 100% relative to an untreated control. Such reduction or prevention in hypertension may be measured by any technique known in the art such as those described herein.

Optionally, the M-RIP inhibitor may be a small molecule antagonist that inhibits the activity of M-RIP or an antisense to M-RIP. RNA interference (RNAi) may also be used to target M-RIP as it provides a powerful method of gene silencing in eukaryotic cells including mammalian cells such as the vascular smooth muscle cells of the present invention. The basic technique of RNAi involves introducing sequence-specific double-stranded RNA into neurons in order to generate a nonheritable, epigenetic knockout of gene function that phenocopies a null mutation in the targeted gene. RNA interference has previously been described (O'Neil N J, et al., *Am J Pharmacogenomics* (2001): 45–53).

Alternatively, the agent that reduces the level or activity of M-RIP may be a dominant negative protein or a nucleic acid encoding a dominant negative protein that interferes with the biological activity of M-RIP (i.e. binding of M-RIP to myosin phosphatase, RhoA, or both). A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative M-RIP may have mutation such that it no longer able to binds myosin phosphatase.

According to this invention, the dominant negative protein may be administered as an expression vector. The expression vector may be a non-viral vector or a viral vector (e.g., retrovirus, recombinant adeno-associated virus, or a recombinant adenoviral vector). Alternatively, the dominant negative protein may be directly administered as a recombinant protein to vascular smooth muscle cells using, for example, microinjection techniques.

The preferred biologically active dose of the therapeutic agent that reduces the level or activity of M-RIP within the practice of the present invention is a dosing that will induce the maximum increase in myosin phosphatase activity and increase in smooth muscle relaxation. Desirably, the therapeutic agent has the ability to reduce the level or activity of M-RIP in smooth muscle cells by at least 5%, 10%, 20%, 30%, 40%, 50%, 60%, 70%, 80%, 90%, or more than 100% below untreated control levels. The levels or activity of M-RIP in vascular smooth muscle cells may be measured by any method known in the art, including, for example, Western blot analysis, immunohistochemistry, ELISA, and Northern Blot analysis. Alternatively, the biological activity of M-RIP can be measured by assessing binding of M-RIP to myosin phosphatase, RhoA, or both. Alternatively, the biological activity of M-RIP may be determined according to its relaxant and contractile effects on vascular rings as described previously by Zhu et al. (*Science* (2002) 5554: 505–8). Preferably, the agent that reduces the level or activity of M-RIP can increase vascular relaxation by at least 5%, 10%, 20%, 30%, 40%, 50%, 60%, 70%, 80%, 90%, or more than 100% above untreated control levels. The agent of the present invention is therefore any agent having any one or more of these activities. Although the agent of the invention is preferably expressed in vascular smooth muscle cells, it is understood that any cell that can influence vascular constriction or relaxation is also amenable to the methods of the invention and include, for example, vascular endothelial cells. Treatment according to the invention is suitable preferably for a human, but may also be administered to other animal species, including for example a monkey, pig, cow, sheep, goat, pig, mouse, rat, dog, or cat.

Second Therapeutic Agents

According to the present invention, the agent that reduces the level or activity of M-RIP is delivered in the mammal in a pharmaceutically acceptable carrier, alone or in combination with one or more anti-hypertensive agents. When the second therapeutic agent is present in a different pharmaceutical composition, different routes of administration may be used. For example, the second therapeutic agent may be administered orally, or by intravenous, intramuscular, or subcutaneous injection. If desired, more than one therapeutic agent may be administered with the agent of the invention and concentrations known to be effective for such therapeutic agents for lowering systemic blood pressure can be used. Desirably, the agent that reduces the level or activity of M-RIP and the anti-hypertensive agent are administered in a single pharmaceutical composition consisting of an effective amount in a pharmaceutically acceptable carrier. Alternatively, the agent of the invention and the second anti-hypertensive agent are administered in separate formulations within at least 1, 2, 4, 6, 10, 12, 18, or more than 24 hours apart. These reagents can be combined and used with additional active or inert ingredients, e.g., in conventional pharmaceutically acceptable carriers. A pharmaceutical carrier can be any compatible, non-toxic substance suitable for the administration of the compositions of the present invention to a mammal. Pharmaceutically acceptable carriers include, for example, water, saline, buffers and other compounds described for example in the Merck Index, Merck & Co., Rahway, N.J. Slow release formulation or a slow release apparatus may be also be used for continuous administration.

Second therapeutic agents may include for example a diuretic, beta blocker, sympathetic nerve inhibitor, vasodilator, alpha-blocker, angiotensin converting enzyme (ACE)

inhibitor, angiotensin II receptor blocker, calcium channel blocker, or vitamin. Examples of diuretics include for example chlorthalidone, furosemide, hydrochlorothiazide, indapamide, metotazone, amiloride, spironolactone, or triamterene and a beta blocker can include acebutolol, amlodipine, amiodarone, atenolol, betaxolol, bisoprolol fumarate, carterolol hydrochloride, metoprolol, mexiletine, moricizine, nadolol, penbutolol, pindolol, procainamide, propranodlol, or timolol. Exemplary sympathetic nerve inhibitors are guanabenz, guanfacine, guanadrel, midodrine, or primidone and a vasodilator may be cyclandelate, hydralazine, or isoxsuprine, minoxidil, nicotynyl, nylidrin, or papaverine. Alpha-blockers, according to the invention, may be doxazosin, prazosin, or terazosin, while angiotensin converting enzyme (ACE) inhibitors may be benazepril, captopril, cilazapril, enalapril, enalaprilat, fosinopril, lisinopril, moexipril, perindopril, quinapril, ramipril, or trandolapril. Typically, angiotensin II receptor blocker are candesartan, eprosartan, irbesarten, losartin, telmisartan, or valsartan, calcium channel blocker are preferably amlodipine, bepridil, diltiazem, felodipine, flunarizine, isradipine, mibefradil, nicardipine, nifedipine, nimodipine, nisoldipine, or verapamil, and vasodilators may be cyclandelate, hydralazine, isoxsuprine, minoxidil, nicotynyl, nylidrin, or papaverine. According to this invention, the M-RIP inhibitor may also be administered with a vitamin such as vitamin A, vitamin $B_1$, $B_2$, $B_6$, $B_{12}$, Vitamin C, Vitamin D, or Vitamin E or alternatively, any other active ingredient having blood pressure lowering action (e.g., high unsaturated fatty acids of omega-3 type, cathechin which is a tea polyphenol or polymer thereof, or rutin). Normally, hydralazine, minodixil, diazoxide, or nitropusside are required only in severe cases of hypertension.

Concentrations of the agent that reduces the level or activity of M-RIP and the second therapeutic agent necessary to reduce blood pressure will depend upon different factors, including means of administration, target site, physiological state of the mammal, and other medication administered. Thus treatment dosages may be titrated to optimize safety and efficacy and is within the skill of an artisan. Determination of the proper dosage and administration regime for a particular situation is within the skill of the art.

In addition to second therapeutic agents, the administration of agent that reduces the levels or activity of M-RIP may also include a modification to the lifestyle of the patient being treated. Such changes may be helpful to control hypertension and include low-fat diet, low sodium diet, stress management, physical exercise, reduction in alcohol intake, or reduction in smoking.

Formulation and Routes of Administration

According to the present invention, the agent that reduces the level or activity of M-RIP may be administered to the mammal by any standard method known in the art. For example, the agent may be administered by means of expression vectors, which encode a dominant negative M-RIP. Such expression vectors may express a nucleic acid sequence substantially identical to the nucleotide sequence of the naturally occurring M-RIP but having reduced activity relative to the naturally occurring M-RIP. Thus, the expression vector may be introduced into suitable host cells capable of producing such a dominant negative molecule.

An expression vector of this invention may be in any of several forms, including, but not limited to, RNA, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein. Preferably, the polynucleotide is DNA and includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. Typically, plasmids are administered to a mammal in an amount of about 1 nanogram to about 5000 micrograms of DNA. Desirably, compositions contain about 5 nanograms to 1000 micrograms of DNA, 10 nanograms to 800 micrograms of DNA, 0.1 micrograms to 500 micrograms of DNA, 1 microgram to 350 micrograms of DNA, 25 micrograms to 250 micrograms of DNA, or 100 micrograms to 200 micrograms of DNA. Alternatively, administration of recombinant adenoviral vectors encoding the M-RIP inhibitor into a mammal may be administered at a concentration of at least $10^5$, $10^6$, $10^7$, $10^8$, $10^9$, $10^{10}$, or $10^{11}$ plaque forming unit (pfu).

Alternatively, the agent of the invention may be administered to the mammal as a recombinant polypeptide. The agent may be directly administered to the vascular smooth muscle cells of a mammal by any standard technique, using for example microinjection techniques. Alternatively, the agent may be administered systematically by any standard route. It is understood that a biological effect may require multiple administration of the agent.

The pharmaceutical compositions according to the present invention are formulated according to the mode of administration to be used. In cases where pharmaceutical compositions are injectable pharmaceutical compositions, they are sterile, pyrogen-free and particulate free. An isotonic formulation is preferably used. Generally, additives for isotonicity can include for example sodium chloride, dextrose, mannitol, sorbitol and lactose. Stabilizers may also be used and include, for example, gelatin and albumin.

Overall, the pharmaceutical composition including the agent that reduces the activity or level or M-RIP can be provided, systemically or locally, by injection (e.g., intrasmuscular, intranasal, intraperitoneal, intradermal, subcutaneous, intravenous, intraarterial, or intraoccular), as well as by oral, topical (e.g., ointment, or patch), or transdermal administration. Alternatively, these compositions may be provided by inhalation, or by suppository. Compositions according to the invention may also be provided to mucosal tissue, by lavage to vaginal, rectal, urethral, buccal, and sublingual tissue for example.

Patients Amenable to Treatment

According to this invention, the administration of an agent that reduces the level or activity of M-RIP is useful to reduce or prevent hypertension in a mammal, preferably a human patient. Diagnosis of hypertension is based on measurements of systemic blood pressure, which is typically reported as a ratio of systolic pressure (arterial pressure during contraction of the heart muscle) to diastolic pressure (residual arterial pressure during relaxation of the heart muscle), reported in units of mmHg. Measurements of blood pressure may be performed by the patient, by a health administrator (e.g., a nurse or a doctor), or any other individual. Typically, blood pressure measurements are repeated over time and considered as an average. Blood pressure measurements can be taken once, twice, three times, or more than three times a day, for a period of at least one day, two days, three days, one week, or more than one week and subsequently considered as an average.

In general, patients amenable to treatment have an elevated blood pressure, suffer from a hypertensive vascular disease, or have an underlying disease or condition predisposing to hypertension. Therefore, patients who have a blood pressure above optimal levels (having a SBP/DBP greater than>120/>80 mmHg) but do not have a hypertensive condition may be administered the M-RIP inhibitor of the invention. If untreated, such a patient may develop various hypertensive conditions, and therefore, reducing the systemic blood pressure in such patients can prevent hypertensive conditions. Typically, blood pressure consistently elevated over 140 systolic (which indicates the pressure generated when the heart beats) or 90 diastolic (which indicates the pressure when the hearts is at rest) is considered to be high. Although such patients do not necessarily have to have any diseases associated with hypertension, they may display symptoms of hypertension. Typically, symptoms associated with hypertension include headaches particularly those affecting the occipital region, dizziness, palpitations, easy fatigability, and impotence. Preferably, the diastolic or the systolic blood pressure, or both are decreased by 5%, 10%, 20%, 30%, 40%, 50%, 60%, 70%, 80%, or more than 90% from the initial blood pressure measurements before treatment.

In more severe cases, patients who have hypertension and who have also been diagnosed with hypertensive conditions may also be administered with the agent of the present invention.

According to this invention, the administration of an agent that reduces the level or activity of M-RIP can treat such conditions, or at least reduce the symptoms, the vascular damage or both caused by hypertension. Hypertensive conditions are typically cardiovascular (e.g., cardiac hypertrophy, myocardial infarct, angina pectoris, congestive heart failure, vascular injury, blood vessel spasm, myocardial ischemia, coronary arterial disease such as atherosclerosis and arteriosclerosis, and aortic dissection) cerebrovascular (cerebral infarction, cerebral hemorrhage, brain damage, loss of vision) or renal (kidney damage or failure). Symptoms associated with hypertensive vascular diseases include, for example, epistaxis, hematuria, blurring of vision owing to retinal changes, episodes of weakness or dizziness due to transient cerebral ischemia, angina pectoris and dyspnea due to cardiac failure. According to this invention, treatment can also include prolonging survival as compared to expected survival in the absence of treatment. Overall, treatment of hypertension or hypertensive conditions refers to both therapeutic treatment and prophylactic or preventative measures. Thus, administration of the agent of the invention may be required to prevent the development of high blood pressure in patients at risk and/or to reduce elevated blood pressure, preferably to normal levels. For maintenance of acceptable levels of blood pressure, repeated treatments may be necessary for an extended period of time.

Preferably, upon treatment the diastolic and systolic blood pressure is decreased by 5%, 10%, 20%, 30%, 40%, 50%, 60%, 70%, 80%, or more than 90% from the initial blood pressure measurements. Alternatively, a hypertensive condition has been treated or prevented if symptoms or damage inflicted by hypertension are reduced by at least 5%, 10%, 20%, 30%, 40%, 50%, 60%, 70%, 80%, more than 90%, or even 100% as measured by any standard technique. For example, diagnosis and monitoring of hypertensive conditions may be based on urine tests; microscopic urinalysis; hematocrits; measurements of blood levels of serum potassium, serum creatinine, and/or blood urea nitrogen, fasting glucose, thyroid stimulating hormone, lipid content (HDL, LDL, cholesterol and TG), serum calcium, and serum phosphate, or total cholesterol; electrocardiogram, echocardiogram, white blood cell count, or chest X-ray. A patient in whom the development of a hypertensive condition is being prevented is one who has not received such a diagnosis according to such techniques. One in the art will understand that these patients may have been subjected to the same tests (electrocardiogram, chest X-ray, etc.) or may have been identified, without examination, as one at high risk due to the presence of one or more risk factors (e.g., family history, hypertension, diabetes mellitus, high cholesterol levels, having a pathological condition predisposing to secondary hypertension). Reduction of hypertensive symptoms or damage may also include, but are not limited to, alleviation of symptoms, diminishment of extent of disease, stabilized (i.e., not worsening) state of disease, delay or slowing of disease progression, and amelioration or palliation of the disease state. Treatment may occur at home with close supervision by the health care provider, or may occur in a health care facility.

As indicated above, the methods of this invention may also be used prophylactically, in patients who are an increased risk of developing a morbid condition associated with hypertension. Risk factors include for example, family history of hypertension or hypertensive conditions, quality of nutrition, level of physical activity, presence of molecular markers of hypertension, age, race, or sex. Patients affected with other non-related disorders may also be predisposed to secondary hypertension. Such disorders include for example adrenal gland tumors, Cushing's syndrome, kidney disorders (e.g., glomreulonephritis, renal vascular obstruction or narrowing, or renal failure), use of medications, drugs or other chemicals (wsuch as oral contraceptives) hemolytic-uremic syndrome, Henoch-Schonlein purpura, periarteritis nodsoa, radiation enteritis, retroperintoneal fibrosis, or Wilms' tumor. In such cases, patients may be treated according to this invention before developing hypertension or a hypertensive condition, or as soon as the risk is identified. Depending on the disorder which may cause secondary hypertension, a number of tests may be used to screen for secondary hypertension. Exemplary diagnostic tests may include measuring angiotensin-converting enzyme inhibitor radionuclide (to detect renovascular disease); 24 hour urine assay to measure levels of creatinine, metanephrines, and catecholamines (to detect phenochromocytoma); overnight dexamethasone suppression test or 24 hour urine measuring cortisol and creatinine levels (to detect Cushing Syndrome) or the plasma aldosterone:renin activity ratio (to detect primary aldosteronism). Renal status may also be evaluated by assessing the presence of protein, blood, and glucose in the urine and measuring serum creatinine and/or blood urea nitrogen.

This invention is based in part on the experiments described in the following examples. These examples are provided to illustrate the invention and should not be construed as limiting.

EXAMPLE 1

Identification and Cloning of M-RIP

To identify proteins involved in regulation of myosin phosphatase, base pairs 2043–3090 of human MBS (MBS-Cterm) were used as bait in a yeast 2-hybrid screen of a human aorta library. Two clones, 6 and 11, encoded the 3' regions of a cDNA with high homology to a murine RhoA-interacting protein, p116RIP3 (Gebbink et al., (1997) *J. Cell Biol.* 137:1603–1613). When retransformed into yeast, both clones interacted with MBS-Cterm but not with the Gal4 DNA binding domain alone. Clone 6 was homologous to base pairs 1617–3072 and clone 11 was homologous to base pairs 2109–3072 of murine p116RIP3.

A human aorta library was next probed for 5' sequence of human p116RIP3. PCR using the human aorta library as a template yielded a 1,686 bp product that was highly homologous to the 5' sequence of murine p116RIP3. The full length human clone was constructed by overlap extension PCR using the yeast 2-hybrid clone 6 and the 5' 1,686 bp sequence (FIG. 1A). The full-length human sequence is 85% identical at the nucleotide level and 90% identical at the amino acid level to murine and rat p116RIP3. The RhoA binding domain of this human clone is 88% identical at the amino acid level to the similar domain on murine p116RIP3. This human cDNA is hereafter called Myosin Phosphatase-Rho Interacting Protein (M-RIP).

Figure 1B:
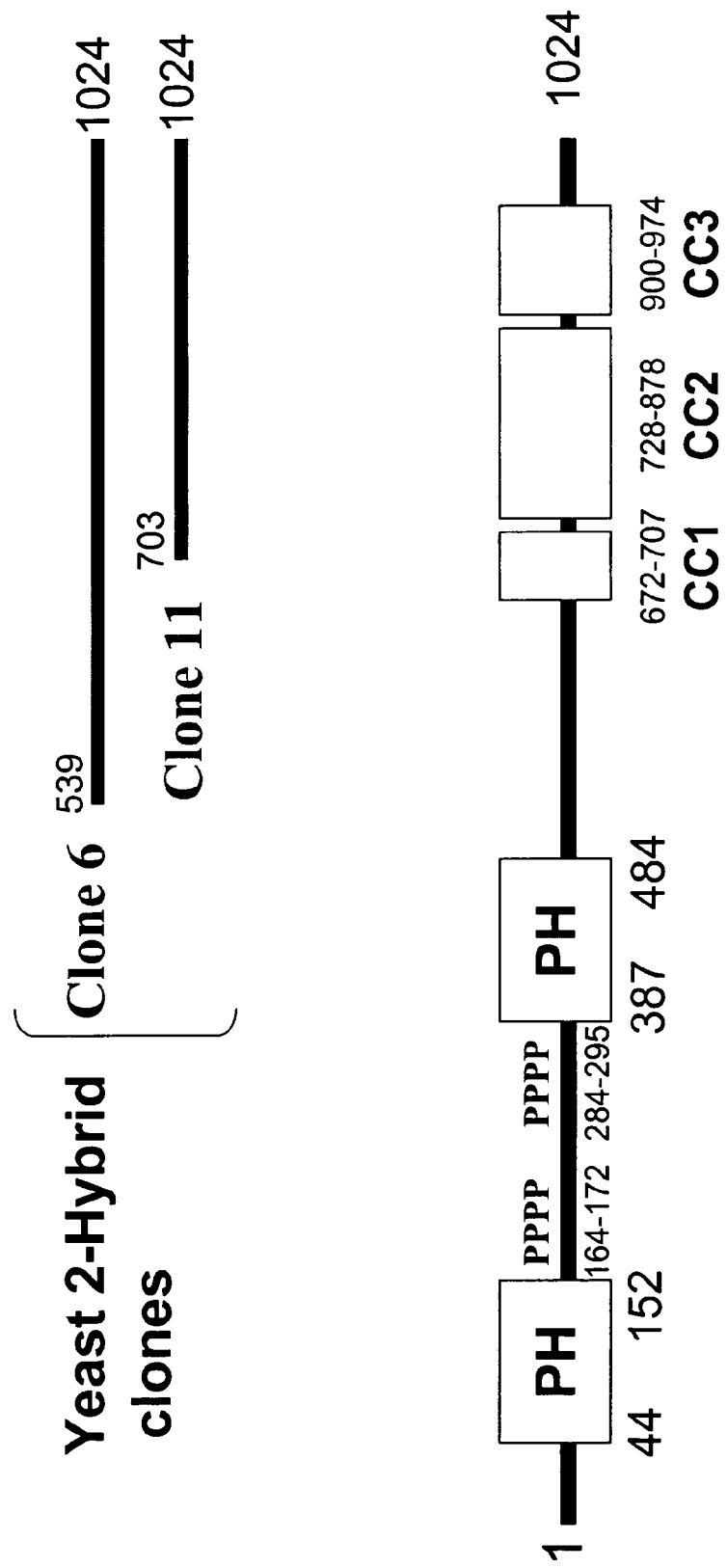
FIG. 1B is a schematic diagram showing the predicted domains of the translated full-length protein product from the M-RIP cDNA. "PH" designates pleckstrin homology domain, "PPPP" designates proline-rich domain, and "CC" designates coiled coil domain. The amino acid numbers corresponding to each domain are shown. Also shown are the corresponding regions of M-RIP encoded by yeast 2-hybrid clones 6 and 11.

Analysis of the M-RIP cDNA predicts a protein of 1,024 amino acids with multiple protein interaction domains, including a pair of pleckstrin homology domains flanking two polyproline motifs, and three carboxy-terminal coiled-coil domains (FIG. 1B). Sites for myristylation as well as for phosphorylation by protein kinase C, cyclic nucleotide-dependent protein kinases and tyrosine kinases are also present in the M-RIP protein.

EXAMPLE 2

Detection and Localization of M-RIP in Vascular Smooth Muscle Cells

Specific MRIP antisera were raised and tested first by immunoblotting of lysates from COS7 cells transfected with full-length M-RIP cDNA. Anti-M-RIP recognized a specific band of 125 kD in untransfected COS7 cells that was augmented by overexpression of full-length MRIP (FIG. 2A). A parallel immunoblot of the same lysates in which anti-M-RIP was pre-absorbed with immunogen failed to identify any M-RIP band. Anti-M-RIP was next used to probe lysates from two different human arterial smooth muscle cell lines. Anti-M-RIP identified a specific 125 kD band in these lysates, supporting that M-RIP is expressed in human vascular smooth muscle cells (FIG. 2B). Although M-RIP from vascular smooth muscle cells was completely insoluble at 250 mM NaCl, it was solubilized and immunoprecipitated under high ionic strength conditions (FIG. 2C).

Cultured human coronary artery smooth muscle cells were immunostained with anti-M-RIP (FIG. 2D, left panel) and with phalloidin (FIG. 2D, middle panel) to label actin fibers. M-RIP localized primarily in a filamentous pattern in the cytoplasm, similar to the distribution of actin filaments. Overlay of the two images revealed that M-RIP co-localized with actin myofilaments (FIG. 2D, right panel). In control experiments, M-RIP antibody pre-incubated with M-RIP immunogen failed to label VSMCs. Despite the presence of a putative nuclear localization signal between residues 151 and 156, M-RIP was not detected in the nucleus of vascular smooth muscle cells.

EXAMPLE 3

In Vivo Interaction Between M-RIP and Myosin Phosphatase

To explore whether the interaction between M-RIP and MBS detected in yeast occurs in intact vascular smooth muscle cells, immunoprecipitation experiments were performed with human aortic smooth muscle cell lysates. Immunoprecipitation of either M-RIP or MBS led to recovery of both proteins (FIG. 3A), supporting an in vivo interaction between M-RIP and MBS in vascular smooth muscle cells. Furthermore, M-RIP immunoprecipitation also led to recovery of PP1 and cGMP-dependent protein kinase (FIG. 3B,C), supporting the hypothesis that M-RIP is associated with the myosin phosphatase complex in vivo. In GST-pulldown interaction studies, binding between M-RIP and either PP1 or cGMP-dependent protein kinase could not be detected, indicating that M-RIP interacts with these proteins indirectly via their known interactions with MBS.

EXAMPLE 4

Characterization of Binding Between M-RIP and Myosin Phosphatase

The M-RIP and MBS interaction was explored further using GST- and His-fusion protein interaction studies. GST-fusions of various M-RIP domains were incubated with vascular smooth muscle cell lysates and recovered MBS was detected by immunoblotting. The individual coiled-coil domains of M-RIP were tested for binding to MBS (FIG. 1C). The second coiled-coil domain (CC2) of M-RIP bound MBS strongly, whereas the CC1 and CC3 domains had little or no interaction with MBS (FIG. 4A). The CC2 domain includes the carboxy-terminal end of the putative Rho-binding domain for murine p116RIP3 (Gebbink et al., supra).

To determine whether MBS binds within the M-RIP RhoA-binding domain, GST-fusion proteins were constructed for the M-RIP RhoA-binding domain (GST-M-RIP545-823, which excludes the carboxy-terminus of CC2), and for the M-RIP RhoA-binding domain plus the remaining carboxy-terminus of CC2 (GST-M-RIP545-878), and tested for binding of MBS from vascular smooth muscle cell lysates (FIG. 4B). GST-M-RIP545-823, failed to bind MBS from the lysate, whereas both GST-M-RIP728-878 (CC2) and GST-M-RIP545-878 bound MBS. Identical results were obtained in heterologous expression studies with epitope-tagged constructs for various M-RIP domains expressed in COS1 cells (FIG. 4B). These data indicate that MBS binds a domain of M-RIP distinct from and 3' to the Rho-binding domain (FIG. 4C).

The carboxy-terminus of MBS contains a leucine zipper domain that mediates binding to other coiled-coil domains, including the leucine/isoleucine zipper domain of cGMPde-pendent protein kinase 1α (Surks et al., (1999) *Science* 286:1583–1587; Khatri et al., (2001) *J.Biol.Chem.* 276: 37250–37257; Surks et al., (2003) *Cell. Signal.* 15:937–944). To determine if this domain of MBS mediates binding to the CC2 of M-RIP, wild type C terminal MBS (MBSLZ) and mutant Cterminal MBS in which all leucines in the leucine zipper domain were mutated to alanine (MBSLZmutant), were expressed as GST-fusion proteins and tested for binding to fulllength M-RIP. Wild type GST-MBSLZ interacted with M-RIP whereas GSTMB-SLZmutant bound no appreciable M-RIP from the same lysates (FIG. 4D). Full-length GFP-MBS or full-length GFP-MBSLZ mutant also was studied in COS1 cells known to express endogenous MBS. GST-M-RIP545-878 bound both endogenous MBS and GFP-MBS, but failed to bind GFP-MBSLZ mutant (FIG. 4E), supporting further that the M-RIP-MBS interaction is mediated by the CC2 of M-RIP and the leucine zipper domain of MBS.

Direct binding between M-RIP and MBS was also tested (FIG. 4F). GST-MBSLZ bound HisCC2, but not HisCC1 or HisCC3, demonstrating that the CC2 of M-RIP binds directly to MBS, while GST-MBSLZ mutant did not interact with any of the coiled coil domains, confirming that the MBS leucine zipper domain mediates the interaction.

EXAMPLE 5

M-RIP-RhoA Interactions

Recombinant HisRhoA was used to test whether M-RIP binds RhoA. Both GDPβS- and GTPγS-RhoA bound M-RIP expressed in COS1 cells (FIG. 5A). In direct binding assays, RhoA, loaded in vitro with GDPβS or GTPγS, was incubated with GST-Rhotekin Rho-binding domain (RhotekinRBD, positive control), GST-M-RIP545-823 or GST-M-RIP545-878. GST-RhotekinRBD bound Rho-GTP preferentially (Ren et al., *Academic Press. Regulators and Effectors of Small GTPases. Balch*, (2000) 325:265–270) whereas both GST-M-RIP545-823 and GST-M-RIP545-878 bound HisRhoA, without preference for GDP or GTP binding state of the low molecular weight G-protein (FIG. 5B).

Our results indicate that M-RIP assembles a complex including the Myosin Binding Subunit (MBS) of myosin phosphatase and RhoA. In particular, RhoA binds an M-RIP domain that includes amino acids 545-823 (FIG. 5B) while MBS binds a domain that includes amino acids 823–878 (FIGS. 4B and 4C). An M-RIP construct containing both domains was expressed in COS1 cells and used to test the hypothesis that this region of M-RIP assembles a ternary complex of M-RIP with MBS and RhoA (FIG. 5C). RhoA bound equally well to GST-M-RIP545-823 and to GSTM-RIP545-878, though MBS did not bind to GST-M-RIP545-823. These data support that amino acids 545-878 of M-RIP, via adjacent RhoA and MBS binding domains, mediates binding of both RhoA and MBS, and that MBS binding is not required for the binding of RhoA to M-RIP (FIG. 5C).

Our results also show that M-RIP is associated with RhoA/Rho-kinase in vivo. RhoA and Rho-kinase have been shown to colocalize with actin stress fibers, and are present in stress fiber preparations made by glycerol extraction, but are lost from stress fibers extracted with Triton X (Katoh et al., (2001) *J.Cell Biol.* 153:569–583; Chen et al., (2002) *J.Biol.Chem.* 277:12680–12688). When Triton and Glycerol extracted stress fibers from vascular smooth muscle cells were examined by immunoblot, both contained actin, MBS and M-RIP, whereas glycerol extracted stress fibers, but not Triton extracted stress fibers, also contained RhoA and Rho-kinase (FIG. 6A). Immunostaining of glycerol-extracted vascular smooth muscle cells revealed colocalization of M-RIP, MBS and RhoA with actin stress fibers (FIG. 6B). Because of the requirement of detergent and high ionic strength conditions for MRIP solubilization, RhoA could not be detected in the M-RIP immunopellet by immunoblot. However, the M-RIP immunopellet contained kinase activity (FIG. 6C) that was inhibited 45% (P=0.005, n=3) by the Rho-kinase inhibitor Y27632 (FIG. 6D) supporting an association between M-RIP and RhoA/Rho-kinase in vivo.

Overall, we have identified M-RIP, a protein that is expressed in human vascular myocytes and that is bound to myosin phosphatase. Immunostaining experiments show that M-RIP colocalizes with actin myofilaments, consistent with p116RIP3 binding to actin. M-RIP is thus localized to the contractile filament where myosin light chain phosphorylation regulates contractile state, therefore implicating M-RIP in myosin phosphatase regulation. The amino terminus of M-RIP contains adjacent pleckstrin homology domains and polyproline motifs, a structural combination also found on Bruton's tyrosine kinase where it mediates binding to both actin and Gα12. This region of p116RIP3 mediates actin binding and actin bundling activity in vitro. Whereas p116RIP3 has been noted to be present in the cell nucleus, we could not detect endogenous M-RIP in the nucleus of vascular smooth muscle cells, implying either a difference in localization between the murine and human homologs, or cell type-specific nuclear localization.

The C-terminal domain of M-RIP interacts with both MBS and RhoA. The RhoA-binding domain of M-RIP overlaps the amino-terminal 95 amino acids of CC2, suggesting an indirect interaction between M-RIP and MBS via RhoA. However, we have found that both RhoA and MBS bind M-RIP directly to separate and adjacent domains (amino acids 545–823 for RhoA and 823–878 for MBS). Our data therefore supports a model where M-RIP binding brings MBS and RhoA into proximity (FIG. 7). The C-terminal domain of MBS contains a leucine zipper domain that mediates binding to a leucine/isoleucine zipper in cGMP-dependent protein kinase 1α. Here, we show that the MBS leucine zipper domain also binds the C-terminal fifty five amino acids of the M-RIP CC2 domain. Thus the same domain of MBS binds to both proteins. MBS may therefore bind M-RIP and cGMP-dependent protein kinase 1α simultaneously because M-RIP can interact with cGMP-dependent protein kinase 1α, as shown by coimmunoprecipitation, without evidence of direct binding, suggesting that the interaction occurs indirectly with MBS as the intermediary protein.

Using both purified protein interaction studies and cell lysates, we found that M-RIP binds RhoA directly and independently of nucleotide binding state. The high ionic strength and detergents required to solubilize and immunoprecipitate M-RIP would be expected to disrupt binding to RhoA and Rho-kinase (Katoh et al, supra). However, using a glycerol extraction method shown to preserve RhoA and Rho-kinase localization to stress fibers (Katoh et al, supra) we found that M-RIP copurified with RhoA and Rho-kinase. Immunostaining of glycerolextracted coronary myocytes confirmed that stress fiber architecture and colocalization of M-RIP, MBS and RhoA with these structures was preserved. Furthermore, despite the presence of detergent and high ionic strength, Rho-kinase activity could be detected in the M-RIP immunopellet due to the high sensitivity of autoradiography. Coupled with the in vitro direct binding studies, these data strongly support that M-RIP interacts with RhoA in vivo.

In summary, M-RIP, the human homolog of p116RIP3, binds myosin phosphatase and RhoA in vascular smooth muscle cells. Our binding studies support a model where M-RIP brings MBS and RhoA into proximity (FIG. 7).

The binding to myosin phosphatase and RhoA and localization to actin myofilaments indicate that M-RIP may target RhoA to the myosin phosphatase complex to regulate myosin phosphorylation state.

The above experiments were performed using the following materials and methods.

MATERIALS AND METHODS

Vectors pGBT9, and pGAD424, Yeast Strain Y190 and Human Aorta

The Matchmaker cDNA library was obtained from Clontech. Vector pCMV-Tag was obtained from Stratagene. All enzymes were from New England Biolabs. Y27632 was from Tocris. pGEX vectors were from Pharmacia, pQE vectors from Qiagen and pCI mammalian expression vector was from Promega. The TA cloning system was from Invitrogen.

Antibodies were obtained as follows: anti-MYPT1 from Covance, anti-RhoA, anti-GSTand anti-PP1 from Santa Cruz Biotechnology, M2 antibody from Sigma, anti-cGMP-dependent protein kinase from Stressgen and anti-ROKα from Transduction Labs.

Cell Culture

All cells were maintained in DME with 10% fetal bovine serum. COS-7 cells were from the American Type Culture Collection. Human aortic and coronary smooth muscle cells were cultured by the explant method. Ao184 and Co399 cells were immortalized using adenovirus expressing E6 and E7 and selection for G418 resistance. Transfections were performed by electroporation.

Yeast 2-Hybrid Screening

Human MBS-Cterm, base pairs 2043–3090 (kind gift of Dr. Masaaki Ito) was cloned into the EcoR1 site of yeast 2-hybrid vectors pGBT9 and pGAD424, expressing MBS fusion proteins with Gal4 DNA binding domain and DNA activating domain, respectively. Expression of MBS-Cterm in yeast was confirmed by dimerization when MBS-Cterm-pGBT9 and MBS-Cterm-pGAD424 were coexpressed in yeast (data not shown). Yeast strain Y190 was sequentially transformed with MBSCterm- pGBT9 and a human aorta cDNA library (Clontech) using the lithium acetate method. Interactions were identified by growth on selective media, and confirmed by colony lift filter β-galactosidase assay. The cDNA library plasmid was extracted from confirmed positive yeast colonies, and sequenced at the Tufts Core Sequencing Facility.

Cloning of Full Length M-RIP

Primers were designed to amplify the 5' sequence of MRIP. The 5' primer was based on a human EST which is homologous to the 5' sequence of mouse and rat p116RIP3, gb AI 678749 (5' ACC ATG TCG GCA GCC AAG GAG AAC CCG TGC 3' (SEQ ID NO: 3)). The 3' primer was based on sequence within yeast 2-hybrid clone 6 (5' CCG CTC CTG AGC CAG GGC CTG CTG GAT GGG 3' (SEQ ID NO: 4)). The 5' M-RIP sequence was amplified from the human aorta cDNA library. The PCR product was ligated into pCRII using the TA cloning system and sequenced. Full-length M-RIP was generated by overlap-extension PCR using 5' M-RIP (bp 1–1686) and yeast 2-hybrid clone 6 (bp 1599–3076) alone for the first 5 cycles, then adding M-RIP 5' and 3' primers (5' ACC ATG TCG GCA GCC AAG GAG AAC CCG TGC 3' (SEQ ID NO: 5)and 5' ATT TCA GGT ATC CCA CGA GAC CTG CTC AAT 3' (SEQ ID NO: 6)) for 25 cycles. The PCR product was ligated into pCRII using the TA cloning system. Full length M-RIP was sequenced in both directions (Genbank accession #AY296247).

DNA Constructs

Full-length M-RIP with an amino-terminal Flag tag was constructed as follows: Amino-terminal M-RIP was amplified from full-length M-RIP using primers 8 which incorporated a 5' Flag sequence (5' GAT GAA TTC CGA CCA TGG ACT ACA AGG ACG ACG ATG ACA AGT CGG CAG CCA AGG AGA ACC CGT GCA GG 3' (SEQ ID NO: 7) and 5' CCG CTC CTG AGC CAG GGC CTG CTG GAT GGG 3' (SEQ ID NO: 8)) and the PCR product which included the amino-terminal half of M-RIP was cloned into mammalian expression vector pCI. All but the Flag-tagged amino terminus of M-RIP was replaced by adding the Age1/Not1 fragment from wild-type M-RIP to generate full-length Flag-tagged MRIP. M-RIP coiled coil domains were amplified from full-length M-RIP using the following primers: CC1: 5' TGC GGT CGA CCT CGC ACG TGG CCT GCA GCA CGT AGC C 3' (SEQ ID NO: 9) and 5' TGC GGT CGA CCT CCC GGC CCA GGG CCA CCC TCA GCT G 3' (SEQ ID NO: 10), CC2: 5' CCG GAA TTC CGA GGG TTT GCA GCA ATG GAA GAA ACG 3' (SEQ ID NO: 11) and 5' TGC GGT CGA CAG TCA GCA GCG TCC GCA ACC GTG TGA T 3' (SEQ ID NO: 12), CC3: 5' CCG GAA TTC GCC TAT GAA CTA GAG GTC TTA TTG CGG 3' (SEQ ID NO: 13) and 5' TGC GGT CGA CGG GGA CTT CTC CCC CAG TGC TTC CGT T 3' (SEQ ID NO: 14). PCR products were cloned into pGEX and pQE vectors for expression as GST and polyhistidine fusion proteins, respectively. M-RIP545-823 and M-RIP545-878 were amplified from full length MRIP by PCR using the following primers. M-RIP545-823: 5' CGCGGATCC GCT GAG TTC CGT CCC ATC CAG CAG (SEQ ID NO: 15) and 3' GGCGAATTC CCG AGA GGA CCA CCA GTT CCC GC (SEQ ID NO: 16). M-RIP545-878 was amplified using the 5' M-RIP545-823 primer and the 3' CC2 primer. Both PCR products were cloned into pGEX and pCMV-Tag2B (Clontech) vectors for expression of GST-fusion proteins in bacteria and Flag-tagged proteins in mammalian cells respectively. Wild-type Flag-RhoA cDNA and GST-RhotekinRBD were kind gifts of Dr. Naoki Mochizuki. RhoA was cloned into pQE for expression of polyhistidine-tagged RhoA in bacteria. RhotekinRBD includes amino acids 1–99 of 9 mouse Rhotekin (Reid et al., (1996) *J.Biol.Chem.* 271:13556–13560), amplified by PCR from a mouse cDNA library and ligated into pGEX4T-3. GST-MBSLZ (amino acids 847–1030) was made as described (Surks et al, supra). GSTMBSLZmutant was made as described (Surks et al., supra). GFP-MBS was prepared by amplifying full-length human MBS from the Clontech human aorta library, followed by ligation into pEGFP. GFP-MBSLZM was prepared by replacing the C-terminal domain of GFP-MBS with the C-terminal domain of GST-MBSLZmutant. All DNA constructs were fully sequenced in both directions.

Production of Anti-M-RIP Antisera cDNA encoding the 5' 480 bp of M-RIP was amplified from full-length M-RIP using PCR primers: 5' ATC GAA TTC ATG TCG GCA GCC AAG GAG AAC 3' (SEQ ID NO: 17) and 5' CGA TCC TCG AGC TTC TTC TGA TTC TGC TTG TT 3' (SEQ ID NO: 18). The PCR product was ligated into pGEX and sequenced. The GST-fusion protein of N-terminal M-RIP (RIP 1–160) was expressed in and purified from bacteria as described (Surks et al., supra). GST-RIP 1–160 was eluted from glutathione agarose beads and specific rabbit antiserum was produced at Alpha Diagnostic International, San Antonio Tex. Crude antisera were purified on protein A beads as described (Harlow et al., (1988) *Antibodies, A Laboratory Manual*).

Preparation of Fusion Proteins

GST- and 6×his-fusion proteins were grown in bacteria overnight at 37° C. in LB with 150 µg/ml ampicillin. The culture was diluted ten fold with LB/Amp, and incubated an additional 1 hour. IPTG was added to a final concentration of 0.1 mM for GST-fusion proteins and 1 mM for 6×his-fusion proteins, and the cells were incubated 4 hours, pelleted and frozen. For GST-fusion proteins, the cell pellet was thawed and resuspended in 35 ml of 20 mM Tris pH 8, 100 mM NaCl, 1.5 mM EDTA, 10 0.1% sarkosyl, 0.25 mg/ml lysozyme, 2 mM PMSF, 10 mM benzamidine, 20 mM DTT and 0.01 μg/ml each of aprotinin, leupeptin and pepstatin A. The cell lysate was incubated on ice for 15 minutes, then EDTA and sarkosyl were added to final concentrations of 5 mM and 1.4%, respectively. The lysate was sonicated, centrifuged and to the supernatant was added 20 ml of 10% Triton X and glutathione-agarose beads. This was incubated for 2 hrs at 4° C., following which the beads were washed with cold PBS. GST-fusion proteins were either stored at 4° C. bound to glutathione agarose beads, or eluted from beads in 50 mM Tris pH 8.0 and 15 mM reduced glutathione, snap frozen and stored at −80° C. For 6×his-fusion proteins, the bacterial pellet was resuspended in lysis buffer consisting of 50 mM NaH2PO4pH 8.0, 300 mM NaCl, 10 mM Imidazole, 0.01 μg/ml each of aprotinin, leupeptin and pepstatin A, 2mM PMSF. Lysozyme was added to a final concentration of 1mg/ml and incubated for 30 minutes on ice. The lysate was then sonicated and centrifuged at 12,500 rpm for 20minutes. The supernatant was incubated with 0.5 ml of Ni-NTA beads (Qiagen) for two hours, then washed with lysis buffer. 6×his fusion proteins were then stored at 40C bound to Ni-NTA beads, or eluted from the beads in 50 mM Tris pH 8.0, 150 mM NaCl, 5mM MgCl2, 1 mM DTT and 250 mM imidazole, snap frozen and stored at −80° C.

Purification and Loading of 6×hisRhoA

The procedure was based on that of Diekmann and Hall (Diekmann et al., (1995) Academic Press. Small GTPases and Their Regulators 256:207–215.). Briefly, 6×hisRhoA was purified as described above for 6×his-fusion proteins. Eluted 6×hisRhoA was dialyzed in 10 mM Tris pH 7.5, 150mnM NaCl, 2 mM MgCl2 and 0. lmM DTT, then snap frozen. Two μg of purified 6×his RhoA was loaded in 50 mM Tris 7.5, 5 mM EDTA and 0.5 mg/ml BSA with either 200 μM GTPγS or GDPβS 11 for 15 minutes at room temperature, followed by the addition of MgCl2 to a final concentration of 60 mM.

Solubility Assay

Subconfluent cultured human aortic smooth muscle cells were rinsed twice with cold PBS and lysed in 50 mM Tris pH 7.5, 1 mM EDTA, 0.5% NP40, 2 mM PMSF, 0.01 μg/ml each of aprotinin, leupeptin and pepstatin A, and NaCl, 250 or 350 mM. Lysates were incubated one hour at room temperature, then centrifuged at 14,000 rpm for 20 minutes. The supernatant fraction was precleared with protein A beads, then used for immunoprecipitation with polyclonal anti-M-RIP antibody as described below. An equivalent percentage of each fraction was analyzed by anti-M-RIP immunoblot.

Co-immunoprecipitation Assays

Confluent cultured human aortic smooth muscle cells were rinsed in PBS, then lysed in buffer A (50 mM Tris pH 7.6, 7 mM MgCl2, 2 mM EDTA, 2 mg/ml n-Dodecyl-B-maltoside, 0.4 mg/ml cholesteryl hemisuccinate, 0.6 M NaCl, 10 mM sodium molybdate, 2 mMPMSF, and 0.01 μg/ml each of aprotinin, leupeptin and pepstatin A) for MBS immunoprecipitations and in buffer B (40 mM Tris pH 7.5, 0.275 M NaCl, 4 mM EDTA, 2% Triton X, 20% glycerol, 50 mM β-glycerol phosphate, 2 mM PMSF, and 0.01 μg/ml each of aprotinin, leupeptin and pepstatin A) for M-RIP and cGMP-dependent protein kinase immunoprecipitations. Cell lysates were incubated one hour at room temperature, then centrifuged at 14,000 rpm for 20 minutes at 40C. The supernatant was precleared with protein A beads and incubated overnight with either polyclonal anti-M-RIP, anti-MBS or anti-cGMP-dependent protein kinase 1. Protein A 12 beads were added, and the lysates were incubated 2 hours. The beads were washed three times with buffer C (50 mM Tris pH 7.6, 7 mM MgCl2, 2 mM EDTA), then proteins were eluted in SDS sample buffer and analyzed by SDS-PAGE and immunoblotting as above.

For co-immunoprecipitation of MBS with Flag-M-RIP domains, COS1 cells were transfected by electroporation, and lysates prepared with buffer A as above after 48 hours. Immunoprecipitations were performed as above except that M2 antibody was used for immunoprecipitation, and protein G beads were used to collect antigen-antibody complexes.

Fusion Protein Interaction Assays

For fusion protein interactions with proteins from cell lysates, confluent cells were rinsed twice with ice cold PBS, lysed in buffer A, incubated for 1 hour at room temperature, then centrifuged at 14,000 rpm for 20 minutes at 40C. The supernatant was mixed with GST-fusion proteins prebound to glutathione agarose beads. After overnight incubation at 40C, the beads were washed with buffer C, eluted with SDS sample buffer and bound proteins were analyzed by immunoblotting. For fusion protein interactions with purified proteins, fusion proteins immobilized on beads were incubated in buffer A for one hour with purified soluble protein previously eluted from beads. After incubation, the beads were washed three times with buffer C, bound proteins were eluted in SDS sample buffer and analyzed by immunoblotting with anti-GST antibodies.

Stress Fiber Preparation

Stress fiber preparation was prepared as follows (adapted from Katoh et al (Katoh et al., supra). Human aortic smooth muscle cells were grown on two 100 mm dishes to near confluence, washed with cold PBS, then 13 extracted with 10 ml of TEA extraction buffer (2.5 mM TEA, 1 μg/ml leupeptin and pepstatin A, 20 μg/ml aprotinin) for 30 minutes, shaking, with replacement of extraction buffer every 2–3 minutes. Remaining cell components were then further extracted using 10 ml of Triton buffer (0.5% Triton ×100, 1 μg/ml of leupeptin and pepstatin A, 20 μg/ml of aprotinin in PBS) for Triton extractions or 10 ml of Glycerol buffer (50% glycerol, 1 μg/ml each of leupeptin and pepstatin A, 20 μg/ml aprotinin in PBS) for glycerol extractions for 5 minutes while shaking, with replacement of extraction buffer twice.

Triton or glycerol was then removed by washing with 10 ml aprotinin-PBS (20 μg/ml aprotinin, 1 μg/ml of leupeptin and pepstatin A in PBS) for 10 minutes while shaking with one replacement of wash buffer. Remaining insoluble material was then scraped in aprotinin-PBS, and homogenized with a Z-shaped 21 gauge needle. The insoluble debris was pelleted at 1000 g for 5 minutes, and stress fibers were isolated by centrifugation of the supernatant at 100,000 g for 1 hour. The stress fiber pellet was boiled in 0.1 ml of protein sample buffer and subjected to SDS-PAGE and immunoblotting with the indicated antibodies. For immunostaining of purified stress fibers, human coronary artery smooth muscle cells were grown on coverslips and glycerol-extracted as described above. Stress fibers were then fixed and immunostained as described below. All antibody dilutions were 1:100.

Kinase Assay

Subconfluent human aortic smooth muscle cells were lysed and M-RIP immunoprecipitated as described for the solubility assay above, with 350 mM NaCl. The M-RIP and nonimmune IPs were washed with Rho-kinase assay buffer (adapted from Feng et al (Feng et al., (1999) *J.Biol.Chem.* 274:3744–3752), 20 mM Tris pH 7.5, 100 mM KCl, 0.1 mM DTT, 5 mM MgCl2, 1 mM 14 EDTA, 1 µM okadaic acid) with or without 1 µM Y27632. After the addition of 20 µCi of 32P-γ-ATP, the samples were incubated for 20 minutes at 30° C. The reaction was stopped by the addition of protein sample buffer, the samples were boiled 5 minutes and then analyzed by SDS-PAGE and autoradiography. The phosphobands were quantitated by densitometry using an Alpha Innotech image analyzer, and graphed using SigmaPlot 5.

Immunofluorescence Staining

Human coronary artery smooth muscle cells were plated on coverslips in DME with 10% fetal bovine serum. The coverslips were washed with PBS twice, then fixed in 3.7% paraformaldehyde. The cells were permeabilized with 0.3% Triton X and 10% donkey serum, then blocked in PBS with 10% donkey serum.

The cells were incubated with 1:400 anti-RIP (Transduction Laboratories) in 10% donkey serum in PBS for 1 hour. After washing in PBS, the cells were incubated in 1:500 donkey anti-mouse IgG conjugated to Cy3 (Jackson ImmunoResearch) and phalloidin-FITC (Sigma) or Alexa Fluor 488-phalloidin (Molecular Probes) in PBS for 1 hour.

Cells were washed in PBS and mounted on glass slides with SlowFade (Molecular Probes).

Amino acid alignments were performed using the BLAST 2 sequences program from the National Center for Biotechnology Information. Protein structure prediction was made using the Simple Modular Architecture Research Tool (http://smart.embl-heidelberg.de/), phosphorylation sites were predicted using Omiga (Oxford Molecular) and nuclear localization signals were predicted using PredictNLS Online (http:H//cubic.bioc.columbia.edu/predictNLS/).

OTHER EMBODIMENTS

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A substantially pure nucleic acid molecule comprising SEQ ID NO: 19 wherein said nucleic acid encodes a polypeptide that binds myosin phosphatase, RhOA or both.

2. The nucleic acid molecule of claim 1, wherein said nucleic acid encodes a human M-RIP protein.

3. The nucleic acid molecule of claim 1, wherein said nucleic acid has the nucleic acid sequence of SEQ ID NO: 19.

4. The nucleic acid molecule of claim 1, wherein said nucleic acid encodes a polypeptide having an amino acid sequence of SEQ ID NO: 1.

* * * * *

UNITED STATES PATENT AND TRADEMARK OFFICE
CERTIFICATE OF CORRECTION

| | |
|---|---|
| PATENT NO. | : 7,122,655 B2 |
| APPLICATION NO. | : 10/715632 |
| DATED | : October 17, 2006 |
| INVENTOR(S) | : Mendelsohn et al. |

It is certified that error appears in the above-identified patent and that said Letters Patent is hereby corrected as shown below:

Column 1,
  Add following CROSS REFERENCE TO RELATED APPLICATIONS section, --STATEMENT AS TO FEDERALLY FUNDED RESEARCH-- ; --This invention was made with support under HL55309 and K08-03987 awarded by the National Institutes of Health. The government has certain rights in the invention. --

Column 3,
  Line 56, replace "metotazone" with --metolazone-- ;
  Line 59, replace "carterolol" with --carteolol-- ;
  Line 61, replace "propranodlol" with --propranolol-- ; and
  Line 64, replace "nicotynyl" with --nicotinyl-- .

Column 4, Line 2, replace "losartin" with --losartan-- .

Column 8, Line 11, replace "immublot" with --immunoblot-- .

Column 17,
  Line 4, replace "metotazone" with --metolazone-- ;
  Line 7, replace "carterolol" with --carteolol-- ;
  Line 9, replace "propranodlol" with --propranolol-- ;
  Line 12, replace "nicotynyl" with --nicotinyl-- ;
  Line 19, replace "losartin" with --losartan-- ;
  Line 24, replace "nicotynyl" with --nicotinyl-- ; and
  Line 32, replace "nitropusside" with --nitroprusside-- .

Column 18, Line 42, replace "intrasmuscular" with --intramuscular-- .

UNITED STATES PATENT AND TRADEMARK OFFICE
CERTIFICATE OF CORRECTION

PATENT NO. : 7,122,655 B2
APPLICATION NO. : 10/715632
DATED : October 17, 2006
INVENTOR(S) : Mendelsohn et al.

It is certified that error appears in the above-identified patent and that said Letters Patent is hereby corrected as shown below:

Column 20, Line 33, replace "glomreulonephritis" with
--glomerulonephritis--.

Signed and Sealed this

Twenty-first Day of August, 2007

JON W. DUDAS
*Director of the United States Patent and Trademark Office*

SEQUENCE LISTING

<160> NUMBER OF SEQ ID NOS: 20

<210> SEQ ID NO 1
<211> LENGTH: 1024
<212> TYPE: PRT
<213> ORGANISM: Homo sapien

<400> SEQUENCE: 1

```
Met Ser Ala Ala Lys Glu Asn Pro Cys Arg Lys Phe Gln Ala Asn Ile
 1               5                  10                  15

Phe Asn Lys Ser Lys Cys Gln Asn Cys Phe Lys Pro Arg Glu Pro His
                20                  25                  30

Leu Leu Asn Asp Glu Asp Leu Thr Gln Ala Lys Pro Ile Tyr Gly Gly
            35                  40                  45

Trp Leu Leu Leu Ala Pro Asp Gly Thr Asp Phe Asp Asn Pro Val His
    50                  55                  60

Arg Ser Arg Lys Trp Gln Arg Arg Phe Phe Ile Leu Tyr Glu His Gly
65                  70                  75                  80

Leu Leu Arg Tyr Ala Leu Asp Glu Met Pro Thr Thr Leu Pro Gln Gly
                85                  90                  95

Thr Ile Asn Met Asn Gln Cys Thr Asp Val Val Asp Gly Glu Gly Arg
            100                 105                 110

Thr Gly Gln Lys Phe Ser Leu Cys Ile Leu Thr Pro Glu Lys Glu His
        115                 120                 125

Phe Ile Arg Ala Glu Thr Lys Glu Ile Val Ser Gly Trp Leu Glu Met
    130                 135                 140

Leu Met Val Tyr Pro Arg Thr Asn Lys Gln Asn Gln Lys Lys Lys Arg
145                 150                 155                 160

Lys Val Glu Pro Pro Thr Pro Gln Glu Pro Gly Pro Ala Lys Val Ala
```

-continued

```
                165                 170                 175
Val Thr Ser Ser Ser Ser Ser Ser Ser Ile Pro Ser Ala
            180                 185                 190
Glu Lys Val Pro Thr Thr Lys Ser Thr Leu Trp Gln Glu Glu Met Arg
            195                 200                 205
Thr Lys Asp Gln Pro Asp Gly Ser Ser Leu Ser Pro Ala Gln Ser Pro
            210                 215                 220
Ser Gln Ser Gln Pro Ala Ala Ser Ser Leu Arg Glu Pro Gly Leu
225                 230                 235                 240
Glu Ser Lys Glu Glu Ser Ala Met Ser Ser Asp Arg Met Asp Cys
            245                 250                 255
Gly Arg Lys Val Arg Val Glu Ser Gly Tyr Phe Ser Leu Glu Lys Thr
            260                 265                 270
Lys Gln Asp Leu Lys Ala Glu Glu Gln Leu Pro Pro Leu Ser
            275                 280                 285
Pro Pro Ser Pro Ser Thr Pro Asn His Arg Arg Ser Gln Val Ile Glu
            290                 295                 300
Lys Phe Glu Ala Leu Asp Ile Glu Lys Ala Glu His Met Glu Thr Asn
305                 310                 315                 320
Ala Val Gly Pro Ser Pro Ser Ser Asp Thr Arg Gln Gly Arg Ser Glu
            325                 330                 335
Lys Arg Ala Phe Pro Arg Lys Arg Asp Phe Thr Asn Glu Ala Pro Pro
            340                 345                 350
Ala Pro Leu Pro Asp Ala Ser Ala Ser Pro Leu Ser Pro His Arg Arg
            355                 360                 365
Ala Lys Ser Leu Asp Arg Arg Ser Thr Glu Pro Ser Val Thr Pro Asp
            370                 375                 380
Leu Leu Asn Phe Lys Lys Gly Trp Leu Thr Lys Gln Tyr Glu Asp Gly
385                 390                 395                 400
Gln Trp Lys Lys His Trp Phe Val Leu Ala Asp Gln Ser Leu Arg Tyr
            405                 410                 415
Tyr Arg Asp Ser Val Ala Glu Glu Ala Ala Asp Leu Asp Gly Glu Ile
            420                 425                 430
Asp Leu Ser Ala Cys Tyr Asp Val Thr Glu Tyr Pro Val Gln Arg Asn
            435                 440                 445
Tyr Gly Phe Gln Ile His Thr Lys Glu Gly Glu Phe Thr Leu Ser Ala
            450                 455                 460
Met Thr Ser Gly Ile Arg Arg Asn Trp Ile Gln Thr Ile Met Lys His
465                 470                 475                 480
Val His Pro Thr Thr Ala Pro Asp Val Thr Ser Ser Leu Pro Glu Glu
            485                 490                 495
Lys Asn Lys Ser Ser Cys Ser Phe Glu Thr Cys Pro Arg Pro Thr Glu
            500                 505                 510
Lys Gln Glu Ala Glu Leu Gly Glu Pro Asp Pro Glu Gln Lys Thr Ser
            515                 520                 525
Arg Ala Arg Glu Arg Arg Glu Gly Arg Ser Lys Thr Phe Asp Trp
            530                 535                 540
Ala Glu Phe Arg Pro Ile Gln Gln Ala Leu Ala Gln Glu Arg Val Gly
545                 550                 555                 560
Gly Val Gly Pro Ala Asp Thr His Glu Pro Leu Arg Pro Glu Ala Glu
            565                 570                 575
Ser Gly Glu Leu Glu Arg Glu Arg Ala Arg Arg Glu Glu Arg Arg
            580                 585                 590
```

-continued

```
Lys Arg Phe Gly Met Leu Asp Ala Thr Asp Gly Pro Gly Thr Glu Asp
            595                 600                 605

Ala Ala Leu Arg Met Glu Val Asp Arg Ser Pro Gly Leu Pro Met Ser
610                 615                 620

Asp Leu Lys Thr His Asn Val His Val Glu Ile Glu Gln Arg Trp His
625                 630                 635                 640

Gln Val Glu Thr Thr Pro Leu Arg Glu Glu Lys Gln Val Pro Ile Ala
            645                 650                 655

Pro Val His Leu Ser Ser Glu Asp Gly Gly Asp Arg Leu Ser Thr His
                660                 665                 670

Glu Leu Thr Ser Leu Leu Glu Lys Glu Leu Glu Gln Ser Gln Lys Glu
            675                 680                 685

Ala Ser Asp Leu Leu Glu Gln Asn Arg Leu Leu Gln Asp Gln Leu Arg
        690                 695                 700

Val Ala Leu Gly Arg Glu Gln Ser Ala Arg Glu Gly Tyr Val Leu Gln
705                 710                 715                 720

Ala Thr Cys Glu Arg Gly Phe Ala Ala Met Glu Glu Thr His Gln Lys
                725                 730                 735

Lys Ile Glu Asp Leu Gln Arg Gln His Gln Arg Glu Leu Glu Lys Leu
            740                 745                 750

Arg Glu Glu Lys Asp Arg Leu Leu Ala Glu Glu Thr Ala Ala Thr Ile
        755                 760                 765

Ser Ala Ile Glu Ala Met Lys Asn Ala His Arg Glu Glu Met Glu Arg
770                 775                 780

Glu Leu Glu Lys Ser Gln Arg Ser Gln Ile Ser Ser Val Asn Ser Asp
785                 790                 795                 800

Val Glu Ala Leu Arg Arg Gln Tyr Leu Glu Glu Leu Gln Ser Val Gln
                805                 810                 815

Arg Glu Leu Glu Val Leu Ser Glu Gln Tyr Ser Gln Lys Cys Leu Glu
            820                 825                 830

Asn Ala His Leu Ala Gln Ala Leu Glu Ala Glu Arg Gln Ala Leu Arg
        835                 840                 845

Gln Cys Gln Arg Glu Asn Gln Glu Leu Asn Ala His Asn Gln Glu Leu
850                 855                 860

Asn Asn Arg Leu Ala Ala Glu Ile Thr Arg Leu Arg Thr Leu Leu Thr
865                 870                 875                 880

Gly Asp Gly Gly Gly Glu Ala Thr Gly Ser Pro Leu Ala Gln Gly Lys
                885                 890                 895

Asp Ala Tyr Glu Leu Glu Val Leu Leu Arg Val Lys Glu Ser Glu Ile
            900                 905                 910

Gln Tyr Leu Lys Gln Glu Ile Ser Ser Leu Lys Asp Glu Leu Gln Thr
        915                 920                 925

Ala Leu Arg Asp Lys Lys Tyr Ala Ser Asp Lys Tyr Lys Asp Ile Tyr
930                 935                 940

Thr Glu Leu Ser Ile Ala Lys Ala Lys Ala Asp Cys Asp Ile Ser Arg
945                 950                 955                 960

Leu Lys Glu Gln Leu Lys Ala Ala Thr Glu Ala Leu Gly Glu Lys Ser
                965                 970                 975

Pro Asp Ser Ala Thr Val Ser Gly Tyr Asp Ile Met Lys Ser Lys Ser
            980                 985                 990

Asn Pro Asp Phe Leu Lys Lys Asp Arg Ser Cys Val Thr Arg Gln Leu
        995                 1000                1005
```

```
Arg Asn Ile Arg Ser Lys Ser Val Ile Glu Gln Val Ser Trp Asp Thr
    1010                1015                1020
```

<210> SEQ ID NO 2
<211> LENGTH: 1024
<212> TYPE: PRT
<213> ORGANISM: Homo sapien

<400> SEQUENCE: 2

```
Met Ser Ala Ala Lys Glu Asn Pro Cys Arg Lys Phe Gln Ala Asn Ile
  1               5                  10                  15

Phe Asn Lys Ser Lys Cys Gln Asn Cys Phe Lys Pro Arg Glu Ser His
             20                  25                  30

Leu Leu Asn Asp Glu Asp Leu Thr Gln Ala Lys Pro Ile Tyr Gly Gly
         35                  40                  45

Trp Leu Leu Leu Ala Pro Asp Gly Thr Asp Phe Asp Asn Pro Val His
 50                  55                  60

Arg Ser Arg Lys Trp Gln Arg Phe Phe Ile Leu Tyr Glu His Gly
 65                  70                  75                  80

Leu Leu Arg Tyr Ala Leu Asp Glu Met Pro Thr Thr Leu Pro Gln Gly
                 85                  90                  95

Thr Ile Asn Met Asn Gln Cys Thr Asp Val Val Asp Gly Glu Ala Arg
            100                 105                 110

Thr Gly Gln Lys Phe Ser Leu Cys Ile Leu Thr Pro Asp Lys Glu His
            115                 120                 125

Phe Ile Arg Ala Glu Thr Lys Glu Ile Ile Ser Gly Trp Leu Glu Met
        130                 135                 140

Leu Met Val Tyr Pro Arg Thr Asn Lys Gln Asn Gln Lys Lys Arg
145                 150                 155                 160

Lys Val Glu Pro Pro Thr Pro Gln Glu Pro Gly Pro Ala Lys Met Ala
                165                 170                 175

Val Thr Ser Ser Ser Gly Gly Thr Gly Ser Ser Ser Ile Pro
                180                 185                 190

Ser Ala Glu Lys Val Pro Thr Thr Lys Ser Thr Leu Trp Gln Glu Glu
            195                 200                 205

Met Arg Ala Lys Asp Gln Pro Asp Gly Thr Ser Leu Ser Pro Ala Gln
        210                 215                 220

Ser Pro Ser Gln Ser Gln Pro Pro Ala Ala Cys Thr Pro Arg Glu Pro
225                 230                 235                 240

Gly Leu Glu Ser Lys Glu Asp Glu Ser Thr Ile Ser Gly Asp Arg Val
                245                 250                 255

Asp Gly Gly Arg Lys Val Arg Val Glu Ser Gly Tyr Phe Ser Leu Glu
            260                 265                 270

Lys Ala Lys Gln Asp Leu Arg Ala Glu Glu Gln Leu Pro Pro Leu Leu
        275                 280                 285

Ser Pro Pro Ser Pro Ser Thr Pro His Ser Arg Arg Ser Gln Val Ile
    290                 295                 300

Glu Lys Phe Glu Ala Leu Asp Ile Glu Lys Ala Glu His Met Glu Thr
305                 310                 315                 320

Asn Met Leu Ile Leu Thr Thr Pro Ser Ser Asp Thr Arg Gln Gly Arg
                325                 330                 335

Ser Glu Arg Arg Ala Ile Pro Arg Lys Arg Asp Phe Ala Ser Glu Ala
            340                 345                 350

Pro Thr Ala Pro Leu Ser Asp Ala Cys Pro Leu Ser Pro His Arg Arg
        355                 360                 365
```

-continued

```
Ala Lys Ser Leu Asp Arg Arg Ser Thr Glu Ser Ser Met Thr Pro Asp
    370                 375                 380

Leu Leu Asn Phe Lys Lys Gly Trp Leu Thr Lys Gln Tyr Glu Asp Gly
385                 390                 395                 400

Gln Trp Lys Lys His Trp Phe Val Leu Ala Asp Gln Ser Leu Arg Tyr
                    405                 410                 415

Tyr Arg Asp Ser Val Ala Glu Glu Ala Asp Leu Asp Gly Glu Ile
                420                 425                 430

Asn Leu Ser Thr Cys Tyr Asp Val Thr Glu Tyr Pro Val Gln Arg Asn
            435                 440                 445

Tyr Gly Phe Gln Ile His Thr Lys Glu Gly Glu Phe Thr Leu Ser Ala
        450                 455                 460

Met Thr Ser Gly Ile Arg Arg Asn Trp Ile Gln Thr Ile Met Lys His
465                 470                 475                 480

Val Leu Pro Ala Ser Ala Pro Asp Val Thr Ser Ser Leu Pro Glu Gly
                    485                 490                 495

Lys Asn Lys Ser Thr Ser Phe Glu Thr Cys Ser Arg Ser Thr Glu Lys
                500                 505                 510

Gln Glu Ala Glu Pro Gly Glu Pro Asp Pro Glu Gln Lys Lys Ser Arg
            515                 520                 525

Ala Arg Glu Arg Arg Glu Gly Arg Ser Lys Thr Phe Asp Trp Ala
        530                 535                 540

Glu Phe Arg Pro Ile Gln Gln Ala Leu Ala Gln Glu Arg Ala Ser Ala
545                 550                 555                 560

Val Gly Ser Ser Asp Ser Gly Asp Pro Gly Cys Leu Glu Ala Glu Pro
                    565                 570                 575

Gly Glu Leu Glu Arg Glu Arg Ala Arg Arg Glu Glu Pro Arg Lys
                580                 585                 590

Arg Phe Gly Met Leu Asp Thr Ile Asp Gly Pro Gly Met Glu Asp Thr
            595                 600                 605

Ala Leu Arg Met Asp Ile Asp Arg Ser Pro Gly Leu Leu Gly Thr Pro
        610                 615                 620

Asp Leu Lys Thr Gln Asn Val His Val Glu Ile Glu Gln Arg Trp His
625                 630                 635                 640

Gln Val Glu Thr Thr Pro Leu Arg Glu Glu Lys Gln Val Pro Ile Ala
                    645                 650                 655

Pro Leu His Leu Ser Leu Glu Asp Arg Ser Glu Arg Leu Ser Thr His
                660                 665                 670

Glu Leu Thr Ser Leu Leu Glu Lys Glu Leu Glu Gln Ser Gln Lys Glu
            675                 680                 685

Ala Ser Asp Leu Leu Glu Gln Asn Arg Leu Leu Gln Asp Gln Leu Arg
        690                 695                 700

Val Ala Leu Gly Arg Glu Gln Ser Ala Arg Glu Gly Tyr Val Leu Gln
705                 710                 715                 720

Ala Thr Cys Glu Arg Gly Phe Ala Ala Met Glu Glu Thr His Gln Lys
                    725                 730                 735

Lys Ile Glu Asp Leu Gln Arg Gln His Gln Arg Glu Leu Glu Lys Leu
                740                 745                 750

Arg Glu Glu Lys Asp Arg Leu Leu Ala Glu Glu Thr Ala Ala Thr Ile
            755                 760                 765

Ser Ala Ile Glu Ala Met Lys Asn Ala His Arg Glu Glu Met Glu Arg
        770                 775                 780
```

-continued

```
Glu Leu Glu Lys Ser Gln Arg Ser Gln Ile Ser Ser Ile Asn Ser Asp
785                 790                 795                 800

Ile Glu Ala Leu Arg Arg Gln Tyr Leu Glu Leu Gln Ser Val Gln
            805                 810                 815

Arg Glu Leu Glu Val Leu Ser Glu Gln Tyr Ser Gln Lys Cys Leu Glu
            820                 825                 830

Asn Ala His Leu Ala Gln Ala Leu Glu Ala Glu Arg Gln Ala Leu Arg
            835                 840                 845

Gln Cys Gln Arg Glu Asn Gln Glu Leu Asn Ala His Asn Gln Glu Leu
        850                 855                 860

Asn Asn Arg Leu Ala Ala Glu Ile Thr Arg Leu Arg Thr Leu Leu Thr
865                 870                 875                 880

Gly Asp Gly Gly Gly Glu Ser Thr Gly Leu Pro Leu Thr Gln Gly Lys
                    885                 890                 895

Asp Ala Tyr Glu Leu Glu Val Leu Leu Arg Val Lys Glu Ser Glu Ile
            900                 905                 910

Gln Tyr Leu Lys Gln Glu Ile Ser Ser Leu Lys Asp Glu Leu Gln Thr
        915                 920                 925

Ala Leu Arg Asp Lys Lys Tyr Ala Ser Asp Lys Tyr Lys Asp Ile Tyr
    930                 935                 940

Thr Glu Leu Ser Ile Ala Lys Ala Lys Ala Asp Cys Asp Ile Ser Arg
945                 950                 955                 960

Leu Lys Glu Gln Leu Lys Ala Ala Thr Glu Ala Leu Gly Glu Lys Ser
                965                 970                 975

Pro Glu Gly Thr Thr Val Ser Gly Tyr Asp Ile Met Lys Ser Lys Ser
            980                 985                 990

Asn Pro Asp Phe Leu Lys Lys Asp Arg Ser Cys Val Thr Arg Gln Leu
        995                 1000                1005

Arg Asn Ile Arg Ser Lys Ser Val Ile Glu Gln Val Ser Trp Asp Asn
    1010                1015                1020
```

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
accatgtcgg cagccaagga gaacccgtgc                                    30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
ccgctcctga gccagggcct gctggatggg                                    30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5

```
accatgtcgg cagccaagga gaacccgtgc                                    30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
atttcaggta tcccacgaga cctgctcaat                                    30

<210> SEQ ID NO 7
<211> LENGTH: 68
<212> TYPE: DNA
<213> ORGANISM: Artificial Sequence
<220> FEATURE:
<223> OTHER INFORMATION: Primer

<400> SEQUENCE: 7
gatgaattcc gaccatggac tacaaggacg acgatgacaa gtcggcagcc aaggagaacc   60
cgtgcagg                                                            68

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
ccgctcctga gccagggcct gctggatggg                                    30

<210> SEQ ID NO 9
<211> LENGTH: 37
<212> TYPE: DNA
<213> ORGANISM: Artificial Sequence
<220> FEATURE:
<223> OTHER INFORMATION: Primer

<400> SEQUENCE: 9
tgcggtcgac ctcgcacgtg gcctgcagca cgtagcc                            37

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
tgcggtcgac ctcccggccc agggccaccc tcagctg                            37

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
ccggaattcc gagggtttgc agcaatggaa gaaacg                             36

<210> SEQ ID NO 12
<211> LENGTH: 37
```

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12
tgcggtcgac agtcagcagc gtccgcaacc gtgtgat        37

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
ccggaattcg cctatgaact agaggtctta ttgcgg         36

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
tgcggtcgac ggggacttct cccccagtgc ttccgtt        37

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
cgcggatccg ctgagttccg tcccatccag cag            33

<210> SEQ ID NO 16
<211> LENGTH: 32
<212> TYPE: DNA
<213> ORGANISM: Artificial Sequence
<220> FEATURE:
<223> OTHER INFORMATION: Primer

<400> SEQUENCE: 16
ggcgaattcc cgagaggacc accagttccc gc             32

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
atcgaattca tgtcggcagc caaggagaac                30

<210> SEQ ID NO 18
<211> LENGTH: 32
<212> TYPE: DNA
<213> ORGANISM: Artificial Sequence
<220> FEATURE:
<223> OTHER INFORMATION: Primer

<400> SEQUENCE: 18

-continued

| cgatcctcga gcttcttctg attctgcttg tt | 32 |

<210> SEQ ID NO 19
<211> LENGTH: 3075
<212> TYPE: DNA
<213> ORGANISM: Homo sapien

<400> SEQUENCE: 19

| atgtcggcag ccaaggagaa cccgtgcagg aaattccagg ccaacatctt caacaagagc | 60 |
| aagtgtcaga actgcttcaa gccccgcgag ccgcatctgc tcaacgacga ggacctgacg | 120 |
| caggcaaaac ccatttatgg cggttggctg ctcctggctc cagatgggac cgactttgac | 180 |
| aacccagtgc accggtctcg gaaatggcag cgacggttct tcatccttta cgagcacggc | 240 |
| ctcttgcgct acgccctgga tgagatgccc acgaccttc ctcagggcac catcaacatg | 300 |
| aaccagtgca cagatgtggt ggatggggag ggccgcacgg ccagaagtt ctccctgtgt | 360 |
| attctgacgc ctgagaagga gcatttcatc cgggcggaga ccaaggagat cgtcagtggg | 420 |
| tggctggaga tgctcatggt ctatccccgg accaacaagc agaatcagaa aagaaacgg | 480 |
| aaagtggagc cccccacacc acaggagcct gggcctgcca aggtggctgt taccagcagc | 540 |
| agcagcagca gcagcagcag cagcatcccc agtgctgaga agtccccac caccaagtcc | 600 |
| acactctggc aggaagaaat gaggaccaag gaccagccag atggcagcag cctgagtcca | 660 |
| gctcagagtc ccagccagag ccagcctcct gctgccagct ccctgcggga acctgggcta | 720 |
| gagagcaaag aagaggagag cgccatgagt acgaccgca tggactgtgg ccgcaaagtc | 780 |
| cgggtggaga gcggctactt ctctctggag aagaccaaac aggacttgaa ggctgaagaa | 840 |
| cagcagctgc ccccgccgct ctcccctccc agcccagca ccccaacca caggaggtcc | 900 |
| caggtgattg aaaagtttga ggccttggac attgagaagg cagagcacat ggagaccaat | 960 |
| gcagtggggc cctcaccatc cagcgacaca cgccagggcc gcagcgagaa gagggcgttc | 1020 |
| cctaggaagc gggacttcac caatgaagcc cccccagctc ctctcccaga cgcctcggct | 1080 |
| tccccccctgt ctccacaccg aagagccaag tcactggaca ggaggtccac ggagccctcc | 1140 |
| gtgacgcccg acctgctgaa tttcaagaaa ggctggctga ctaagcagta tgaggacggc | 1200 |
| cagtggaaga acactggtt tgtcctcgcc gatcaaagcc tgagatacta cagggattca | 1260 |
| gtggctgagg aggcagccga cttggatgga gaaattgact tgtccgcatg ttacgatgtc | 1320 |
| acagagtatc cagtccagag aaactatggc ttccagatac atacaaagga gggcgagttt | 1380 |
| accctgtcgg ccatgacatc tgggattcgg cggaactgga tccagaccat catgaagcac | 1440 |
| gtgcacccga ccactgcccc ggatgtgacc agctcgttgc cagaggaaaa aaacaagagc | 1500 |
| agctgctctt ttgagacctg cccgaggcct actgagaagc aagaggcaga gctggggggag | 1560 |
| ccggaccctg agcagaagac gagccgcgca cgggagcgga ggcgagaggg ccgctccaag | 1620 |
| acctttgact gggctgagtt ccgtcccatc cagcaggccc tggctcagga gcgggtgggc | 1680 |
| ggcgtggggc ctgctgacac ccacgagccc ctgcgccctg aggcggagtc tggggagctg | 1740 |
| gagcgggagc gtgcacggag gcgggaggag cgccgcaagc gcttcgggat gctcgacgcc | 1800 |
| acagacgggc caggcactga ggatgcagcc ctgcgcatgg aggtggaccg gagcccaggg | 1860 |
| ctgcctatga gcgacctcaa aacgcataac gtccacgtgg agattgagca gcggtggcat | 1920 |
| caggtggaga ccacacctct ccgggaagag aagcaggtgc ccatcgcccc cgtccacctg | 1980 |
| tcttctgaag atgggggtga ccggctctcc acacacgagc tgacctctct gctcgagaag | 2040 |
| gagctggagc agagccagaa ggaggcctca gaccttctgg agcagaaccg gctcctgcag | 2100 |

-continued

```
gaccagctga gggtggccct gggccgggag cagagcgccc gtgagggcta cgtgctgcag    2160
gccacgtgcg agcgagggtt tgcagcaatg aagaaacgc accagaagaa gattgaagat     2220
ctccagaggc agcaccagcg ggagctagag aaacttcgag aagagaaaga ccgcctccta    2280
gccgaggaga cagcggccac catctcagcc atcgaagcca tgaagaacgc ccaccgggag    2340
gaaatggagc gggagctgga gaagagccag cggtcccaga tcagcagcgt caactcggat    2400
gttgaggccc tgcggcgcca gtacctggag gagctgcagt cggtgcagcg ggaactggag    2460
gtcctctcgg agcagtactc gcagaagtgc ctggagaatg cccatctggc ccaggcgctg    2520
gaggccgagc ggcaggccct gcggcagtgc cagcgtgaga accaggagct caatgcccac    2580
aaccaggagc tgaacaaccg cctggctgca gagatcacac ggttgcggac gctgctgact    2640
ggggacggcg gtggggaggc cactgggtca ccccttgcac agggcaagga tgcctatgaa    2700
ctagaggtct tattgcgggt aaaggaatcg gaaatacagt acctgaaaca ggagattagc    2760
tccctcaagg atgagctgca gacggcactg cgggacaaga agtacgcaag tgacaagtac    2820
aaagacatct acacagagct cagcatcgcg aaggctaagg ctgactgtga catcagcagg    2880
ttgaaggagc agctcaaggc tgcaacggaa gcactggggg agaagtcccc tgacagtgcc    2940
acggtgtccg gatatgatat aatgaaatct aaaagcaacc ctgacttctt gaagaaagac    3000
agatcctgtg tcacccggca actcagaaac atcaggtcca gtccgtaat  tgagcaggtc    3060 tcgtgggata cctga                                                     3075
```

<210> SEQ ID NO 20
<211> LENGTH: 932
<212> TYPE: PRT
<213> ORGANISM: Homo sapien

<400> SEQUENCE: 20

```
Met Ser Ala Ala Lys Glu Asn Pro Cys Arg Lys Phe Gln Ala Asn Ile
 1               5                  10                  15

Phe Asn Lys Ser Lys Cys Gln Asn Cys Phe Lys Pro Arg Glu His Leu
            20                  25                  30

Leu Asn Asp Glu Asp Leu Thr Gln Ala Lys Pro Ile Tyr Gly Gly Trp
        35                  40                  45

Leu Leu Leu Ala Pro Asp Gly Thr Asp Phe Asp Asn Pro Val His Arg
    50                  55                  60

Ser Arg Lys Trp Gln Arg Arg Phe Phe Ile Leu Tyr Glu His Gly Leu
65                  70                  75                  80

Leu Arg Tyr Ala Leu Asp Glu Met Pro Thr Thr Leu Pro Gln Gly Thr
                85                  90                  95

Ile Asn Met Asn Gln Cys Thr Asp Val Val Asp Gly Glu Arg Thr Gly
            100                 105                 110

Gln Lys Phe Ser Leu Cys Ile Leu Thr Pro Lys Glu His Phe Ile Arg
        115                 120                 125

Ala Glu Thr Lys Glu Ile Ser Gly Trp Leu Glu Met Leu Met Val Tyr
    130                 135                 140

Pro Arg Thr Asn Lys Gln Asn Gln Lys Lys Arg Lys Val Glu Pro
145                 150                 155                 160

Pro Thr Pro Gln Glu Pro Gly Pro Ala Lys Ala Val Thr Ser Ser Ser
                165                 170                 175

Ser Ser Ser Ile Pro Ser Ala Glu Lys Val Pro Thr Thr Lys Ser Thr
            180                 185                 190
```

-continued

```
Leu Trp Gln Glu Glu Met Arg Lys Asp Gln Pro Asp Gly Ser Leu Ser
        195                 200                 205
Pro Ala Gln Ser Pro Ser Gln Ser Gln Pro Pro Ala Ala Arg Glu Pro
    210                 215                 220
Gly Leu Glu Ser Lys Glu Ser Ser Asp Arg Asp Gly Arg Lys Val
225                 230                 235                 240
Arg Val Glu Ser Gly Tyr Phe Ser Leu Glu Lys Lys Gln Asp Leu Ala
                245                 250                 255
Glu Glu Gln Leu Pro Pro Leu Ser Pro Pro Ser Pro Ser Thr Pro Arg
            260                 265                 270
Arg Ser Gln Val Ile Glu Lys Phe Glu Ala Leu Asp Ile Glu Lys Ala
        275                 280                 285
Glu His Met Glu Thr Asn Pro Ser Ser Asp Thr Arg Gln Gly Arg Ser
    290                 295                 300
Glu Arg Ala Pro Arg Lys Arg Asp Phe Glu Ala Pro Ala Pro Leu Asp
305                 310                 315                 320
Pro Leu Ser Pro His Arg Arg Ala Lys Ser Leu Asp Arg Arg Ser Thr
                325                 330                 335
Glu Ser Thr Pro Asp Leu Leu Asn Phe Lys Lys Gly Trp Leu Thr Lys
            340                 345                 350
Gln Tyr Glu Asp Gly Gln Trp Lys Lys His Trp Phe Val Leu Ala Asp
        355                 360                 365
Gln Ser Leu Arg Tyr Tyr Arg Asp Ser Val Ala Glu Ala Ala Asp
    370                 375                 380
Leu Asp Gly Glu Ile Leu Ser Cys Tyr Asp Val Thr Glu Tyr Pro Val
385                 390                 395                 400
Gln Arg Asn Tyr Gly Phe Gln Ile His Thr Lys Glu Gly Glu Phe Thr
                405                 410                 415
Leu Ser Ala Met Thr Ser Gly Ile Arg Arg Asn Trp Ile Gln Thr Ile
            420                 425                 430
Met Lys His Val Pro Ala Pro Asp Val Thr Ser Ser Leu Pro Glu Lys
        435                 440                 445
Asn Lys Ser Ser Phe Glu Thr Cys Arg Thr Glu Lys Gln Glu Ala Glu
    450                 455                 460
Gly Glu Pro Asp Pro Glu Gln Lys Ser Arg Ala Arg Glu Arg Arg Arg
465                 470                 475                 480
Glu Gly Arg Ser Lys Thr Phe Asp Trp Ala Glu Phe Arg Pro Ile Gln
                485                 490                 495
Gln Ala Leu Ala Gln Glu Arg Val Gly Asp Pro Glu Ala Glu Gly Glu
            500                 505                 510
Leu Glu Arg Glu Arg Ala Arg Arg Glu Gly Arg Lys Arg Phe Gly
        515                 520                 525
Met Leu Asp Asp Gly Pro Gly Glu Asp Ala Leu Arg Met Asp Arg Ser
    530                 535                 540
Pro Gly Leu Asp Leu Lys Thr Asn Val His Val Glu Ile Glu Gln Arg
545                 550                 555                 560
Trp His Gln Val Glu Thr Thr Pro Leu Arg Glu Glu Lys Gln Val Pro
                565                 570                 575
Ile Ala Pro His Leu Ser Glu Asp Arg Leu Ser Thr His Glu Leu Thr
            580                 585                 590
Ser Leu Leu Glu Lys Glu Leu Glu Gln Ser Gln Lys Glu Ala Ser Asp
        595                 600                 605
Leu Leu Glu Gln Asn Arg Leu Leu Gln Asp Gln Leu Arg Val Ala Leu
```

```
              610             615             620
Gly Arg Glu Gln Ser Ala Arg Glu Gly Tyr Val Leu Gln Ala Thr Cys
625                 630                 635                 640

Glu Arg Gly Phe Ala Ala Met Glu Glu Thr His Gln Lys Lys Ile Glu
                645                 650                 655

Asp Leu Gln Arg Gln His Gln Arg Glu Leu Glu Lys Leu Arg Glu Glu
                660                 665                 670

Lys Asp Arg Leu Leu Ala Glu Glu Thr Ala Ala Thr Ile Ser Ala Ile
            675                 680                 685

Glu Ala Met Lys Asn Ala His Arg Glu Glu Met Glu Arg Glu Leu Glu
690                 695                 700

Lys Ser Gln Arg Ser Gln Ile Ser Ser Asn Ser Asp Glu Ala Leu Arg
705                 710                 715                 720

Arg Gln Tyr Leu Glu Glu Leu Gln Ser Val Gln Arg Glu Leu Glu Val
                725                 730                 735

Leu Ser Glu Gln Tyr Ser Gln Lys Cys Leu Glu Asn Ala His Leu Ala
                740                 745                 750

Gln Ala Leu Glu Ala Glu Arg Gln Ala Leu Arg Gln Cys Gln Arg Glu
            755                 760                 765

Asn Gln Glu Leu Asn Ala His Asn Gln Glu Leu Asn Asn Arg Leu Ala
770                 775                 780

Ala Glu Ile Thr Arg Leu Arg Thr Leu Leu Thr Gly Asp Gly Gly Gly
785                 790                 795                 800

Glu Thr Gly Pro Leu Gln Gly Lys Asp Ala Tyr Glu Leu Glu Val Leu
                805                 810                 815

Leu Arg Val Lys Glu Ser Glu Ile Gln Tyr Leu Lys Gln Glu Ile Ser
            820                 825                 830

Ser Leu Lys Asp Glu Leu Gln Thr Ala Leu Arg Asp Lys Lys Tyr Ala
            835                 840                 845

Ser Asp Lys Tyr Lys Asp Ile Tyr Thr Glu Leu Ser Ile Ala Lys Ala
850                 855                 860

Lys Ala Asp Cys Asp Ile Ser Arg Leu Lys Glu Gln Leu Lys Ala Ala
865                 870                 875                 880

Thr Glu Ala Leu Gly Glu Lys Ser Pro Thr Val Ser Gly Tyr Asp Ile
                885                 890                 895

Met Lys Ser Lys Ser Asn Pro Asp Phe Leu Lys Lys Asp Arg Ser Cys
                900                 905                 910

Val Thr Arg Gln Leu Arg Asn Ile Arg Ser Lys Ser Val Ile Glu Gln
            915                 920                 925

Val Ser Trp Asp
        930
```